United States Patent [19]
Yue et al.

[11] Patent Number: 6,130,077
[45] Date of Patent: Oct. 10, 2000

[54] HUMAN CYTOCHROME P450

[75] Inventors: Henry Yue, Sunnyvale; Karl J. Guegler, Menlo Park; Neil C. Corley, Mountain View; Janice Au-Young, Berkeley, all of Calif.

[73] Assignee: Incyte Pharmaceuticals, Inc., Palo Alto, Calif.

[21] Appl. No.: 09/165,241

[22] Filed: Oct. 1, 1998

[51] Int. Cl.$^7$ ...................................................... C12N 9/02
[52] U.S. Cl. ..................... 435/189; 536/23.2; 435/320.1; 435/6; 435/252.3; 435/254.11
[58] Field of Search .................. 435/189, 320.1, 435/6, 207.33; 536/23.2

[56] References Cited

U.S. PATENT DOCUMENTS 5,886,157 3/1999 Guengerich et al. .................... 435/189

OTHER PUBLICATIONS

GenBank Accession No. AA580329, Sep. 1997.
GenBank Accession No. AA393407, Apr. 1997.
GenBank Accession No. N78537, Mar. 1996.
GenBank Accession No. AA094256, Oct. 1996.
ExPASY Enzyme: EC 1.14.14.1 (Sep., 1998).
Prosite: PDOC00081 Cytochrome P450 cysteine heme–iron ligand signature (Nov., 1997).
Prints EP4501 E–Class P450 Group I signature (Mar., 1996).
Graham–Lorence, S. and J.A. Peterson, "P450s: Structural similarities and functional differences," *FASEB J.*, 10:206–214 (1996).
Nebert, D.W. and F.J. Gonzalez, "P450 Genes: Structure, Evolution, and Regulation," *Ann. Rev. Biochem.*, 56:945–993 (1987).
Dogra, S.C. et al., "Transcriptional Activation of Cytochrome P450 Genes by Different Classes of Chemical Inducers," *Clin. Exp. Pharmacol. Physiol.*, 25:1–9 (1998).
Online Mendelian Inheritance in Man (OMIM) *601771 Cytochrome P450, Subfamily I (Dioxin–Inducible), Polypeptide 1; CYP1B1 (Apr., 1997).
Katsung, B.G., Ed., *Basic and Clinical Pharmacology*, Appleton & Lange, Norwalk, CT, pp. 48–59 (1995).
Morgan, E.T., "Regulation of Cytochromes P450 During Inflammation and Infection," *Drug Metab. Rev.*, 29(4):1129–1188 (1997).
OMIM *240300 Autoimmune Polyendocrinopathy–Candidiasis–Ectodermal Dystrophy (Jun., 1986).
Isselbacher, K.J. et al., *Harrison's Principles of Internal Medicine*, McGraw–Hill, Inc., New York, NY, pp. 1968–1970 (1994).
Takeyama, K. et al., "25–Hydroxyvitamin $D_3$ 1α–Hydroxylase and Vitamin D Synthesis," *Science*, 227:1827–1830 (1997).
Kitanaka, S. et al., "Inactivating Mutations in the 25–Hydroxyvitamin $D_3$ 1α–Hydroxylase Gene in Patients with Pseudovitamin D–Deficiency Rickets," *N. Engl. J. Med.*, 338(10):653–661 (1998).
OMIM *213700 Cerebrotendinous Xanthomatosis (Jun., 1986).
OMIM #122700 Coumarin Resistance (Jun., 1986).
Agarwal, V.R. et al., "Molecular Basis of Severe Gynecomastia Associated with Aromatase Expression in a Fibrolamellar Hepatocellular Carcinoma," *J. Clin. Endocrinol. Metab.*, 83(5):1797–1800 (1998).
Waxman, D.J., "P450–Catalyzed Steroid Hydroxylation: Assay and Product Indentification by Thin–Layer Chromatography," *Methods Enzymol.*, 206:462–476 (1991).

*Primary Examiner*—Ponnathapu Achutamurthy
*Assistant Examiner*—Kathleen Kerr
*Attorney, Agent, or Firm*—Incyte Pharmaceuticals, Inc.

[57] ABSTRACT

The invention provides a human cytochrome P450 (HUCYP) and polynucleotides which identify and encode HUCYP. The invention also provides expression vectors, host cells, antibodies, agonists, and antagonists. The invention also provides methods for diagnosing, treating, or preventing disorders associated with expression of HUCYP.

11 Claims, 5 Drawing Sheets

FIGURE 1A

```
          9              18              27              36              45              54
5' GCC GAT CCG    AGA CGT GGC    TCC CTG GGC    AGA ACC ATG    TTG GAC TTC    GCG ATC
    A   D   P     R   R   G      S   L   G      R   T   M      L   D   F      A   I 63              72              81              90              99             108
   TTC GCC GTT    ACC TTC TTG    CTG GCG TTG    GTG GGA GCC    GTG CTC TAC    CTC TAT CCG
    F   A   V      T   F   L      L   A   L      V   G   A      V   L   Y      L   Y   P 117             126             135             144             153             162
   GCT TCC AGA    CAA GCT GCA    GGA ATT CCA    GGG ATT ACT    CCA ACT GAA    GAA AAA GAT
    A   S   R      Q   A   A      G   I   P      G   I   T      P   T   E      E   K   D 171             180             189             198             207             216
   GGT AAT CTT    CCA GAT ATT    GTG AAT AGT    GGA AGT TTG    CAT GAG TTC    CTG GTT AAT
    G   N   L      P   D   I      V   N   S      G   S   L      H   E   F      L   V   N 225             234             243             252             261             270
   TTG CAT GAG    AGA TAT GGG    CCT GTC GTC    TCC TTC TGG    TTT GGC AGG    CGC CTC GTG
    L   H   E      R   Y   G      P   V   V      S   F   W      F   G   R      R   L   V 279             288             297             306             315             324
   GTT AGT TTG    GGC ACT GTT    GAT GTA CTG    AAG CAG CAT    ATC AAT CCC    AAT AAG ACA
    V   S   L      G   T   V      D   V   L      K   Q   H      I   N   P      N   K   T 333             342             351             360             369             378
   TTG GAC CCT    TTT GAA ACC    ATG CTG AAG    TCA TTA TTA    AGG TAT CAA    TCT GGT GGT
    L   D   P      F   E   T      M   L   K      S   L   L      R   Y   Q      S   G   G
```

```
         387      396      405      414      423      432
GGC AGT GTG AGT GAA AAC CAC ATG AGG AAA AAA TTG TAT GAA AAT GGT GTG ACT
 G   S   V   S   E   N   H   M   R   K   K   L   Y   E   N   G   V   T 441      450      459      468      477      486
GAT TCT CTG AAG AGT AAC TTT GCC CTC CTC CTA AAG CTT TCA GAA TTA TTA
 D   S   L   K   S   N   F   A   L   L   L   K   L   S   E   E   L   L 495      504      513      522      531      540
GAT AAA TGG CTC TCC TAC CCA GAG ACC CAG CAC GTG CCC CTC AGC CAG CAT ATG
 D   K   W   L   S   Y   P   E   T   Q   H   V   P   L   S   Q   H   M 549      558      567      576      585      594
CTT GGT TTT GCT ATG AAG TCT GTT ACA CAG ATG GTA ATG GGT AGT ACA TTT GAA
 L   G   F   A   M   K   S   V   T   Q   M   V   M   G   S   T   F   E 603      612      621      630      639      648
GAT CAG GAA GTC ATT CGC TTC CAG AAG AAT CAT GGC ACA GTT TGG TCT GAG
 D   Q   E   V   I   R   F   Q   K   N   H   G   T   V   W   S   E 657      666      675      684      693      702
ATT GGA AAA GGC TTT CTA GAT GGG TCA CTT GAT AAA AAC ATG ACT CGG AAA AAA
 I   G   K   G   F   L   D   G   S   L   D   K   N   M   T   R   K   K 711      720      729      738      747      756
CAA TAT GAA GAT GCC CTC ATG CAA CTG GAG TCT GTT TTA AGG AAC ATC ATA AAA
 Q   Y   E   D   A   L   M   Q   L   E   S   V   L   R   N   I   I   K
```

FIGURE 1B

```
              765            774            783            792            801            810
GAA CGA AAA GGA AGG AAC TTC AGT CAA CAT ATT TTC ATT GAC TCC TTA GTA CAA
 E   R   K   G   R   N   F   S   Q   H   I   F   I   D   S   L   V   Q 819            828            837            846            855            864
GGG AAC CTT AAT GAC CAA CAG ATC CTA GAA GAC AGT ATG ATA TTT TCT CTG GCC
 G   N   L   N   D   Q   Q   I   L   E   D   S   M   I   F   S   L   A 873            882            891            900            909            918
AGT TGC ATA ATA ACT GCA AAA TTG TGT ACC TGG GCA ATC TGT TTT TTA ACC ACC
 S   C   I   I   T   A   K   L   C   T   W   A   I   C   F   L   T   T 927            936            945            954            963            972
TCT GAA GTT CAA AAA ATA TTA TAT GAA GAG ATA AAC CAA GTT TTT GGA AAT
 S   E   V   Q   K   K   L   Y   E   E   I   N   Q   V   F   G   N 981            990            999           1008           1017           1026
GGT CCT GTT ACT CCA GAG AAA ATT GAG CAG CTC AGA TAT TGT CAG CAT GTG CTT
 G   P   V   T   P   E   K   I   E   Q   L   R   Y   C   Q   H   V   L 1035           1044           1053           1062           1071           1080
TGT GAA ACT GTT CGA ACT GCC AAA CTG ACT CCA GTT TCT GCC CAG CTT CAA GAT
 C   E   T   V   R   T   A   K   L   T   P   V   S   A   Q   L   Q   D 1089           1098           1107           1116           1125           1134
ATT GAA GGA AAA ATT GAC CGA TTT ATT ATT CCT AGA GAG ACC CTC GTC CTT TAT
 I   E   G   K   I   D   R   F   I   I   P   R   E   T   L   V   L   Y
```

FIGURE 1C

```
      1143           1152           1161           1170           1179           1188
GCC CTT GGT GTG GTA CTT CAG GAT CCT AAT ACT TGG CCA TCT CCA CAC AAG TTT
 A   L   G   V   V   L   Q   D   P   N   T   W   P   S   P   H   K   F 1197           1206           1215           1224           1233           1242
GAT CCA GAT CGG TTT GAT GAT GAA TTA GTA ATG AAA ACT TTT TCC TCA CTT GGA
 D   P   D   R   F   D   D   E   L   V   M   K   T   F   S   S   L   G 1251           1260           1269           1278           1287           1296
TTC TCA GGC ACA CAG GAG TGT CCA GAG TTG AGG TTT GCA TAT ATG GTG ACC ACA
 F   S   G   T   Q   E   C   P   E   L   R   F   A   Y   M   V   T   T 1305           1314           1323           1332           1341           1350
GTA CTT CTT AGT GTA TTG AAG GTG AAG AGA CTG CAC CTA CTT TCT GTG GAG GGA CAG
 V   L   L   S   V   L   K   V   K   R   L   H   L   L   S   V   E   G   Q 1359           1368           1377           1386           1395           1404
GTT ATT GAA ACA AAG TAT GAA CTG GTA ACA TCA AGG GAA GAA GCT TGG ATC
 V   I   E   T   K   Y   E   L   V   T   S   R   E   E   A   W   I 1413           1422           1431           1440           1449           1458
ACT GTC TCA AAG AGA TAT TAA AAT TTT ATA CAT TTA AAA TCA TTG TTA AAT TGA
 T   V   S   K   R   Y 1467           1476           1485           1494           1503           1512
TTG AGG AAA ACA ACC ATT TAA AAA AAA TCT ATG TTG AAT CCT TTT ATA AAC CAG
```

FIGURE 1D

```
     1521           1530           1539          1548           1557      1566
TAT CAC TTT GTA ATA TAA ACA CCT ATT TGT ACT TAA TTT TGT AAA TTT GGA TTT 1575           1584           1593          1602           1611      1620
TTA TAT ATC ATA TTT TCT TAA TTC ATT GTA CAC ATT TGA CTT ACT GCA CAG TAT 1629           1638           1647
ATT GAT CAT TTT AAT GGG AAA AAA AAA A 3'
```

FIGURE 1E

SEQUENCE LISTING

```
<160> NUMBER OF SEQ ID NOS: 2

<210> SEQ ID NO 1
<211> LENGTH: 462
<212> TYPE: PRT
<213> ORGANISM: Homo sapiens
<220> FEATURE: -
<223> OTHER INFORMATION: 991729

<400> SEQUENCE: 1

Met Leu Asp Phe Ala Ile Phe Ala Val Thr Phe Leu Leu Ala Leu
 1               5                  10                  15

Val Gly Ala Val Leu Tyr Leu Tyr Pro Ala Ser Arg Gln Ala Ala
                20                  25                  30

Gly Ile Pro Gly Ile Thr Pro Thr Glu Glu Lys Asp Gly Asn Leu
                35                  40                  45

Pro Asp Ile Val Asn Ser Gly Ser Leu His Glu Phe Leu Val Asn
                50                  55                  60

Leu His Glu Arg Tyr Gly Pro Val Val Ser Phe Trp Phe Gly Arg
                65                  70                  75

Arg Leu Val Val Ser Leu Gly Thr Val Asp Val Leu Lys Gln His
                80                  85                  90

Ile Asn Pro Asn Lys Thr Leu Asp Pro Phe Glu Thr Met Leu Lys
                95                 100                 105

Ser Leu Leu Arg Tyr Gln Ser Gly Gly Gly Ser Val Ser Glu Asn
               110                 115                 120

His Met Arg Lys Lys Leu Tyr Glu Asn Gly Val Thr Asp Ser Leu
               125                 130                 135

Lys Ser Asn Phe Ala Leu Leu Leu Lys Leu Ser Glu Glu Leu Leu
               140                 145                 150

Asp Lys Trp Leu Ser Tyr Pro Glu Thr Gln His Val Pro Leu Ser
               155                 160                 165

Gln His Met Leu Gly Phe Ala Met Lys Ser Val Thr Gln Met Val
               170                 175                 180

Met Gly Ser Thr Phe Glu Asp Asp Gln Glu Val Ile Arg Phe Gln
               185                 190                 195

Lys Asn His Gly Thr Val Trp Ser Glu Ile Gly Lys Gly Phe Leu
               200                 205                 210
```

```
Asp Gly Ser Leu Asp Lys Asn Met Thr Arg Lys Lys Gln Tyr Glu
            215                 220                 225

Asp Ala Leu Met Gln Leu Glu Ser Val Leu Arg Asn Ile Ile Lys
            230                 235                 240

Glu Arg Lys Gly Arg Asn Phe Ser Gln His Ile Phe Ile Asp Ser
            245                 250                 255

Leu Val Gln Gly Asn Leu Asn Asp Gln Gln Ile Leu Glu Asp Ser
            260                 265                 270

Met Ile Phe Ser Leu Ala Ser Cys Ile Ile Thr Ala Lys Leu Cys
            275                 280                 285

Thr Trp Ala Ile Cys Phe Leu Thr Thr Ser Glu Glu Val Gln Lys
            290                 295                 300

Lys Leu Tyr Glu Glu Ile Asn Gln Val Phe Gly Asn Gly Pro Val
            305                 310                 315

Thr Pro Glu Lys Ile Glu Gln Leu Arg Tyr Cys Gln His Val Leu
            320                 325                 330

Cys Glu Thr Val Arg Thr Ala Lys Leu Thr Pro Val Ser Ala Gln
            335                 340                 345

Leu Gln Asp Ile Glu Gly Lys Ile Asp Arg Phe Ile Ile Pro Arg
            350                 355                 360

Glu Thr Leu Val Leu Tyr Ala Leu Gly Val Val Leu Gln Asp Pro
            365                 370                 375

Asn Thr Trp Pro Ser Pro His Lys Phe Asp Pro Asp Arg Phe Asp
            380                 385                 390

Asp Glu Leu Val Met Lys Thr Phe Ser Ser Leu Gly Phe Ser Gly
            395                 400                 405

Thr Gln Glu Cys Pro Glu Leu Arg Phe Ala Tyr Met Val Thr Thr
            410                 415                 420

Val Leu Leu Ser Val Leu Val Lys Arg Leu His Leu Leu Ser Val
            425                 430                 435

Glu Gly Gln Val Ile Glu Thr Lys Tyr Glu Leu Val Thr Ser Ser
            440                 445                 450

Arg Glu Glu Ala Trp Ile Thr Val Ser Lys Arg Tyr
            455                 460

<210> SEQ ID NO 2
<211> LENGTH: 1648
<212> TYPE: DNA
<213> ORGANISM: Homo sapiens
<220> FEATURE: -
<223> OTHER INFORMATION: 991729

<400> SEQUENCE: 2
gccgatccga gacgtggctc cctgggcggc agaaccatgt tggacttcgc gatcttcgcc      60
gttaccttct tgctggcgtt ggtgggagcc gtgctctacc tctatccggc ttccagacaa     120
gctgcaggaa ttccagggat tactccaact gaagaaaaag atggtaatct tccagatatt     180
gtgaatagtg aagtttgca tgagttcctg gttaatttgc atgagagata tgggcctgtg      240
gtctccttct ggtttggcag gcgcctcgtg gttagtttgg cactgttga tgtactgaag      300
cagcatatca atcccaataa gacattggac cctttgaaa ccatgctgaa gtcattatta     360
aggtatcaat ctggtggtgg cagtgtgagt gaaaaccaca tgaggaaaaa attgtatgaa     420
aatggtgtga ctgattctct gaagagtaac tttgccctcc tcctaaagct ttcagaagaa     480
ttattagata aatggctctc ctacccagag acccagcacg tgcccctcag ccagcatatg     540
```

-continued

| | | | | | |
|---|---|---|---|---|---|
| cttggttttg | ctatgaagtc | tgttacacag | atggtaatgg | gtagtacatt | tgaagatgat | 600 |
| caggaagtca | ttcgcttcca | gaagaatcat | ggcacagttt | ggtctgagat | tggaaaaggc | 660 |
| tttctagatg | ggtcacttga | taaaaacatg | actcggaaaa | aacaatatga | agatgccctc | 720 |
| atgcaactgg | agtctgtttt | aaggaacatc | ataaaagaac | gaaaaggaag | gaacttcagt | 780 |
| caacatattt | tcattgactc | cttagtacaa | gggaacctta | atgaccaaca | gatcctagaa | 840 |
| gacagtatga | tattttctct | ggccagttgc | ataataactg | caaaattgtg | tacctgggca | 900 |
| atctgttttt | taaccacctc | tgaagaagtt | caaaaaaaat | tatatgaaga | gataaaccaa | 960 |
| gttttttggaa | atggtcctgt | tactccagag | aaaattgagc | agctcagata | ttgtcagcat | 1020 |
| gtgctttgtg | aaactgttcg | aactgccaaa | ctgactccag | tttctgccca | gcttcaagat | 1080 |
| attgaaggaa | aaattgaccg | atttattatt | cctagagaga | ccctcgtcct | ttatgccctt | 1140 |
| ggtgtggtac | ttcaggatcc | taatacttgg | ccatctccac | acaagtttga | tccagatcgg | 1200 |
| tttgatgatg | aattagtaat | gaaaacttttt | tcctcacttg | gattctcagg | cacacaggag | 1260 |
| tgtccagagt | tgaggtttgc | atatatggtg | accacagtac | ttcttagtgt | attggtgaag | 1320 |
| agactgcacc | tactttctgt | ggagggacag | gttattgaaa | caaagtatga | actggtaaca | 1380 |
| tcatcaaggg | aagaagcttg | gatcactgtc | tcaaagagat | attaaaattt | tatacattta | 1440 |
| aaatcattgt | taaattgatt | gaggaaaaca | accatttaaa | aaaaatctat | gttgaatcct | 1500 |
| tttataaacc | agtatcactt | tgtaatataa | acacctattt | gtacttaatt | ttgtaaattt | 1560 |
| ggatttttat | atatcatatt | ttcttaattc | attgtacaca | tttgacttac | tgcacagtat | 1620 |
| attgatcatt | ttaatgggaa | aaaaaaaa | | | | 1648 |

HUMAN CYTOCHROME P450

FIELD OF THE INVENTION

This invention relates to nucleic acid and amino acid sequences of a human cytochrome P450 and to the use of these sequences in the diagnosis, treatment, and prevention of cell proliferative, developmental, autoimmune/inflammatory, and metabolic disorders.

BACKGROUND OF THE INVENTION

Members of the cytochrome P450 superfamily of enzymes catalyze the oxidative metabolism of a variety of substrates, including natural compounds such as steroids, fatty acids, prostaglandins, leukotrienes, and vitamins, as well as drugs, carcinogens, mutagens, and xenobiotics. Cytochrome P450s, also known as P450 heme-thiolate proteins, usually act as terminal oxidases in multi-component electron transfer chains, called P450-containing monooxygenase systems. Specific reactions catalyzed include hydroxylation, epoxidation, N-oxidation, sulfooxidation, N-, S-, and O-dealkylations, desulfation, deamination, and reduction of azo, nitro, and N-oxide groups. These reactions are involved in steroidogenesis of glucocorticoids, cortisols, estrogens, and androgens in animals; insecticide resistance in insects; herbicide resistance and flower coloring in plants; and environmental bioremediation by microorganisms. Cytochrome P450 actions on drugs, carcinogens, mutagens, and xenobiotics can result in detoxification or in conversion of the substance to a more toxic product. Cytochrome P450s are abundant in the liver, but also occur in other tissues. (See ExPASY ENZYME EC 1.14.14.1; Prosite PDOC00081 Cytochrome P450 cysteine heme-iron ligand signature; PRINTS EP450I E-Class P450 Group I signature; and Graham-Lorence, S. and Peterson, J. A. (1996) FASEB J. 10:206–214.)

Four hundred cytochrome P450s have been identified in diverse organisms including bacteria, fungi, plants, and animals (Graham-Lorence, supra). The B-class is found in prokaryotes and fungi, while the E-class is found is found in bacteria, plants, insects, vertebrates, and mammals. Five subclasses or groups are found within the larger family of E-class cytochrome P450s (PRINTS EP450I E-Class P450 Group I signature).

All cytochrome P450s use a heme cofactor and share structural attributes. Most cytochrome P450s are 400 to 530 amino acids in length. The secondary structure of the enzyme is about 70% alpha-helical and about 22% beta-sheet. The region around the heme-binding site in the C-terminal part of the protein is conserved among cytochrome P450s. A ten amino acid signature sequence in this hemeiron ligand region has been identified which includes a conserved cysteine involved in binding the heme iron in the fifth coordination site. In eukaryotic cytochrome P450s, a membrane-spanning region is usually found in the first 15–20 amino acids of the protein, generally consisting of approximately 15 hydrophobic residues followed by a positively charged residue. (See Prosite PDOC0081, supra; Graham-Lorence, supra.)

Cytochrome P450 enzymes are involved in cell proliferation and development. The enzymes have roles in chemical mutagenesis and carcinogenesis by metabolizing chemicals to reactive intermediates that form adducts with DNA (Nebert, D. W. and Gonzalez, F. J. (1987) Ann. Rev. Biochem. 56:945–993). These adducts can cause nucleotide changes and DNA rearrangements that lead to oncogenesis. Cytochrome P450 expression in liver and other tissues is induced by xenobiotics such as polycyclic aromatic hydrocarbons, peroxisomal proliferators, phenobarbital, and the glucocorticoid dexamethasone (Dogra, S. C. et al. (1998) Clin. Exp. Pharmacol. Physiol. 25:1–9). A cytochrome P450 protein may participate in eye development as mutations in the P450 gene CYP1B1 cause primary congenital glaucoma (Online Mendelian Inheritance in Man (OMIM) *601771 Cytochrome P450, subfamily I (dioxin-inducible), polypeptide 1; CYP1B1). Cytochrome P450s are also involved in drug interactions, because the induction of a cytochrome P450 by one drug may affect the metabolism of another drug by the enzyme (Katzung, B. G. (1995) Basic and Clinical Pharmacoloy, Appleton & Lange, Norwalk Conn., pp. 48–59).

Cytochrome P450s are associated with inflammation and infection. Hepatic cytochrome P450 activities are profoundly affected by various infections and inflammatory stimuli, some of which are suppressed and some induced (Morgan, E. T. (1997) Drug Metab. Rev. 29:1129–1188). Effects observed in vivo can be mimicked by proinflammatory cytokines and interferons. Autoantibodies to two cytochrome P450 proteins were found in patients with autoimmune polyenodocrinopathy-candidiasis-ectodermal dystrophy (APECED), a polyglandular autoimmune syndrome (OMIM *240300 Autoimmune polyendocrinopathy-candidiasis-ectodermal dystrophy).

Mutations in cytochrome P450s have been linked to metabolic disorders, including congenital adrenal hyperplasia, the most common adrenal disorder of infancy and childhood; pseudovitamin D-deficiency rickets; cerebrotendinous xanthomatosis, a lipid storage disease characterized by progressive neurologic dysfunction, premature atherosclerosis, and cataracts; and an inherited resistance to the anticoagulant drugs coumarin and warfarin (Isselbacher, K. J. et al. (1994) Harrison's Principles of Internal Medicine, McGraw-Hill, Inc. New York, N.Y., pp. 1968–1970; Takeyama, K. et al. (1997) Science 277:1827–1830; Kitanaka, S. et al. (1998) N. Engl. J. Med. 338:653–661; OMIM *213700 Cerebrotendinous xanthomatosis; and OMIM #122700 Coumarin resistance). Extremely high levels of expression of the cytochrome P450 protein aromatase were found in a fibrolamellar hepatocellular carcinoma from a boy with severe gynecomastia (feminization) (Agarwal, V. R. (1998) J. Clin. Endocrinol. Metab. 83:1797–1800).

The discovery of a new human cytochrome P450 and the polynucleotides encoding it satisfies a need in the art by providing new compositions which are useful in the diagnosis, prevention, and treatment of cell proliferative, developmental, autoimmune/inflammatory, and metabolic disorders.

SUMMARY OF THE INVENTION

The invention is based on the discovery of a new human cytochrome P450 (HUCYP), the polynucleotides encoding HUCYP, and the use of these compositions for the diagnosis, treatment, or prevention of cell proliferative, developmental, autoimmune/inflammatory, and metabolic disorders.

The invention features a substantially purified polypeptide comprising the amino acid sequence of SEQ ID NO:1 or a fragment of SEQ ID NO:1.

The invention further provides a substantially purified variant having at least 90% amino acid sequence identity to the amino acid sequence of SEQ ID NO:1 or a fragment of SEQ ID NO:1. The invention also provides an isolated and purified polynucleotide encoding the polypeptide comprising the amino acid sequence of SEQ ID NO:1 or a fragment of SEQ ID NO:1. The invention also includes an isolated and purified polynucleotide variant having at least 70% polynucleotide sequence identity to the polynucleotide encoding the polypeptide comprising the amino acid sequence of SEQ ID NO:1 or a fragment of SEQ ID NO:1.

The invention further provides an isolated and purified polynucleotide which hybridizes under stringent conditions to the polynucleotide encoding the polypeptide comprising the amino acid sequence of SEQ ID NO:1 or a fragment of SEQ ID NO:1, as well as an isolated and purified polynucleotide having a sequence which is complementary to the polynucleotide encoding the polypeptide comprising the amino acid sequence of SEQ ID NO:1 or a fragment of SEQ ID NO:1.

The invention also provides a method for detecting a polynucleotide in a sample containing nucleic acids, the method comprising the steps of (a) hybridizing the complement of the polynucleotide sequence to at least one of the polynucleotides of the sample, thereby forming a hybridization complex; and (b) detecting the hybridization complex, wherein the presence of the hybridization complex correlates with the presence of a polynucleotide in the sample. In one aspect, the method further comprises amplifying the polynucleotide prior to hybridization.

The invention also provides an isolated and purified polynucleotide comprising the polynucleotide sequence of SEQ ID NO:2 or a fragment of SEQ ID NO:2, and an isolated and purified polynucleotide variant having at least 70% polynucleotide sequence identity to the polynucleotide comprising the polynucleotide sequence of SEQ ID NO:2 or a fragment of SEQ ID NO:2. The invention also provides an isolated and purified polynucleotide having a sequence complementary to the polynucleotide comprising the polynucleotide sequence of SEQ ID NO:2 or a fragment of SEQ ID NO:2.

The invention further provides an expression vector containing at least a fragment of the polynucleotide encoding the polypeptide comprising the sequence of SEQ ID NO:1 or a fragment of SEQ ID NO:1. In another aspect, the expression vector is contained within a host cell.

The invention also provides a method for producing a polypeptide, the method comprising the steps of: (a) culturing the host cell containing an expression vector containing at least a fragment of a polynucleotide under conditions suitable for the expression of the polypeptide; and (b) recovering the polypeptide from the host cell culture.

The invention also provides a pharmaceutical composition comprising a substantially purified polypeptide having the sequence of SEQ ID NO:1 or a fragment of SEQ ID NO:1 in conjunction with a suitable pharmaceutical carrier.

The invention further includes a purified antibody which binds to a polypeptide comprising the sequence of SEQ ID NO:1 or a fragment of SEQ ID NO:1, as well as a purified agonist and a purified antagonist of the polypeptide.

The invention also provides a method for treating or preventing a disorder associated with decreased expression or activity of HUCYP, the method comprising administering to a subject in need of such treatment an effective amount of a pharmaceutical composition comprising a substantially purified polypeptide having the amino acid sequence of SEQ ID NO:1 or a fragment of SEQ ID NO:1, in conjunction with a suitable pharmaceutical carrier.

The invention also provides a method for treating or preventing a disorder associated with increased expression or activity of HUCYP, the method comprising administering to a subject in need of such treatment an effective amount of an antagonist of the polypeptide having the amino acid sequence of SEQ ID NO:1 or a fragment of SEQ ID NO:1.

BRIEF DESCRIPTION OF THE FIGURES AND TABLE

FIGS. 1A, 1B, 1C, 1D, and 1E show the amino acid sequence (SEQ ID NO:1) and nucleic acid sequence (SEQ ID NO:2) of HUCYP. The alignment was produced using MACDNASIS PRO software (Hitachi Software Engineering, South San Francisco Calif.).

Table 1 shows the tools, programs, and algorithms used to analyze HUCYP, along with applicable descriptions, references, and threshold parameters.

DESCRIPTION OF THE INVENTION

Before the present proteins, nucleotide sequences, and methods are described, it is understood that this invention is not limited to the particular machines, materials and methods described, as these may vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a," "an," and "the" include plural reference unless the context clearly dictates otherwise. Thus, for example, a reference to "a host cell" includes a plurality of such host cells, and a reference to "an antibody" is a reference to one or more antibodies and equivalents thereof known to those skilled in the 14 art, and so forth.

Unless defined otherwise, all technical and scientific terms used herein have the same meanings as commonly understood by one of ordinary skill in the art to which this invention belongs. Although any machines, materials, and methods similar or equivalent to those described herein can be used to practice or test the present invention, the preferred machines, materials and methods are now described. All publications mentioned herein are cited for the purpose of describing and disclosing the cell lines, protocols, reagents and vectors which are reported in the publications and which might be used in connection with the invention. Nothing herein is to be construed as an admission that the invention is not entitled to antedate such disclosure by virtue of prior invention.

Definitions

"HUCYP" refers to the amino acid sequences of substantially purified HUCYP obtained from any species, particularly a mammalian species, including bovine, ovine, porcine, murine, equine, and preferably the human species, from any source, whether natural, synthetic, semi-synthetic, or recombinant.

The term "agonist" refers to a molecule which, when bound to HUCYP, increases or prolongs the duration of the effect of HUCYP. Agonists may include proteins, nucleic acids, carbohydrates, or any other molecules which bind to and modulate the effect of HUCYP.

An "allelic variant" is an alternative form of the gene encoding HUCYP. Allelic variants may result from at least one mutation in the nucleic acid sequence and may result in altered mRNAs or in polypeptides whose structure or function may or may not be altered. Any given natural or recombinant gene may have none, one, or many allelic forms. Common mutational changes which give rise to allelic variants are generally ascribed to natural deletions, additions, or substitutions of nucleotides. Each of these types of changes may occur alone, or in combination with the others, one or more times in a given sequence.

"Altered" nucleic acid sequences encoding HUCYP include those sequences with deletions, insertions, or substitutions of different nucleotides, resulting in a polypeptide the same as HUCYP or a polypeptide with at least one functional characteristic of HUCYP. Included within this definition are polymorphisms which may or may not be readily detectable using a particular oligonucleotide probe of the polynucleotide encoding HUCYP, and improper or unexpected hybridization to allelic variants, with a locus other than the normal chromosomal locus for the polynucleotide sequence encoding HUCYP. The encoded protein may also be "altered," and may contain deletions, insertions, or substitutions of amino acid residues which produce a silent change and result in a functionally equivalent HUCYP. Deliberate amino acid substitutions may be made on the basis of similarity in polarity, charge, solubility, hydrophobicity, hydrophilicity, and/or the amphipathic nature of the residues, as long as the biological or immunological activity of HUCYP is retained. For example, negatively charged amino acids may include aspartic acid and glutamic acid, positively charged amino acids may include lysine and arginine, and amino acids with uncharged polar head groups having similar hydrophilicity values may include leucine, isoleucine, and valine; glycine and alanine; asparagine and glutamine; serine and threonine; and phenylalanine and tyrosine.

The terms "amino acid" or "amino acid sequence" refer to an oligopeptide, peptide, polypeptide, or protein sequence, or a fragment of any of these, and to naturally occurring or synthetic molecules. In this context, "fragments," "immunogenic fragments," or "antigenic fragments" refer to fragments of HUCYP which are preferably at least 5 to about 15 amino acids in length, most preferably at least 14 amino acids, and which retain some biological activity or immunological activity of HUCYP. Where "amino acid sequence" is recited to refer to an amino acid sequence of a naturally occurring protein molecule, "amino acid sequence" and like terms are not meant to limit the amino acid sequence to the complete native amino acid sequence associated with the recited protein molecule.

"Amplification" relates to the production of additional copies of a nucleic acid sequence. Amplification is generally carried out using polymerase chain reaction (PCR) technologies well known in the art.

The term "antagonist" refers to a molecule which, when bound to HUCYP, decreases the amount or the duration of the effect of the biological or immunological activity of HUCYP. Antagonists may include proteins, nucleic acids, carbohydrates, antibodies, or any other molecules which decrease the effect of HUCYP.

The term "antibody" refers to intact molecules as well as to fragments thereof, such as Fab, F(ab')$_2$, and Fv fragments, which are capable of binding the epitopic determinant. Antibodies that bind HUCYP polypeptides can be prepared using intact polypeptides or using fragments containing small peptides of interest as the immunizing antigen. The polypeptide or oligopeptide used to immunize an animal (e.g., a mouse, a rat, or a rabbit) can be derived from the translation of RNA, or synthesized chemically, and can be conjugated to a carrier protein if desired. Commonly used carriers that are chemically coupled to peptides include bovine serum albumin, thyroglobulin, and keyhole limpet hemocyanin (KLH). The coupled peptide is then used to immunize the animal.

The term "antigenic determinant" refers to that fragment of a molecule (i.e., an epitope) that makes contact with a particular antibody. When a protein or a fragment of a protein is used to immunize a host animal, numerous regions of the protein may induce the production of antibodies which bind specifically to antigenic determinants (given regions or three-dimensional structures on the protein). An antigenic determinant may compete with the intact antigen (i.e., the immunogen used to elicit the immune response) for binding to an antibody.

The term "antisense" refers to any composition containing a nucleic acid sequence which is complementary to the "sense" strand of a specific nucleic acid sequence. Antisense molecules may be produced by any method including synthesis or transcription. Once introduced into a cell, the complementary nucleotides combine with natural sequences produced by the cell to form duplexes and to block either transcription or translation. The designation "negative" can refer to the antisense strand, and the designation "positive" can refer to the sense strand.

The term "biologically active," refers to a protein having structural, regulatory, or biochemical functions of a naturally occurring molecule. Likewise, "immunologically active" refers to the capability of the natural, recombinant, or synthetic HUCYP, or of any oligopeptide thereof, to induce a specific immune response in appropriate animals or cells and to bind with specific antibodies.

The terms "complementary" or "complementarity" refer to the natural binding of polynucleotides by base pairing. For example, the sequence "5' A-G-T 3'" bonds to the complementary sequence "3' T-C-A 5'." Complementarity between two single-stranded molecules may be "partial," such that only some of the nucleic acids bind, or it may be "complete," such that total complementarity exists between the single stranded molecules. The degree of complementarity between nucleic acid strands has significant effects on the efficiency and strength of the hybridization between the nucleic acid strands. This is of particular importance in amplification reactions, which depend upon binding between nucleic acids strands, and in the design and use of peptide nucleic acid (PNA) molecules.

A "composition comprising a given polynucleotide sequence" or a "composition comprising a given amino acid sequence" refer broadly to any composition containing the given polynucleotide or amino acid sequence. The composition may comprise a dry formulation or an aqueous solution. Compositions comprising polynucleotide sequences encoding HUCYP or fragments of HUCYP may be employed as hybridization probes. The probes may be stored in freeze-dried form and may be associated with a stabilizing agent such as a carbohydrate. In hybridizations, the probe may be deployed in an aqueous solution containing salts (e.g., NaCl), detergents (e.g., sodium dodecyl sulfate; SDS), and other components (e.g., Denhardt's solution, dry milk, salmon sperm DNA, etc.). "Consensus sequence" refers to a nucleic acid sequence which has been resequenced to resolve uncalled bases, extended using XL-PCR kit (Perkin-Elmer, Norwalk Conn.) in the 5' and/or the 3' direction, and resequenced, or which has been assembled from the overlapping sequences of more than one Incyte Clone using a computer program for fragment assembly, such as the GEL-VIEW Fragment Assembly system (GCG, Madison Wis.). Some sequences have been both extended and assembled to produce the consensus sequence.

The term "correlates with expression of a polynucleotide" indicates that the detection of the presence of nucleic acids, the same or related to a nucleic acid sequence encoding HUCYP, by northern analysis is indicative of the presence of nucleic acids encoding HUCYP in a sample, and thereby correlates with expression of the transcript from the polynucleotide encoding HUCYP.

A "deletion" refers to a change in the amino acid or nucleotide sequence that results in the absence of one or more amino acid residues or nucleotides.

The term "derivative" refers to the chemical modification of a polypeptide sequence, or a polynucleotide sequence. Chemical modifications of a polynucleotide sequence can include, for example, replacement of hydrogen by an alkyl, acyl, or amino group. A derivative polynucleotide encodes a polypeptide which retains at least one biological or immunological function of the natural molecule. A derivative polypeptide is one modified by glycosylation, pegylation, or any similar process that retains at least one biological or immunological function of the polypeptide from which it was derived.

The term "similarity" refers to a degree of complementarity. There may be partial similarity or complete similarity. The word "identity" may substitute for the word "similarity." A partially complementary sequence that at least partially inhibits an identical sequence from hybridizing to a target nucleic acid is referred to as "substantially similar." The inhibition of hybridization of the completely complementary sequence to the target sequence may be examined using a hybridization assay (Southern or northern blot, solution hybridization, and the like) under conditions of reduced stringency. A substantially similar sequence or hybridization probe will compete for and inhibit the binding of a completely similar (identical) sequence to the target sequence under conditions of reduced stringency. This is not to say that conditions of reduced stringency are such that non-specific binding is permitted, as reduced stringency conditions require that the binding of two sequences to one another be a specific (i.e., a selective) interaction. The absence of non-specific binding may be tested by the use of a second target sequence which lacks even a partial degree of complementarity (e.g., less than about 30% similarity or identity). In the absence of non-specific binding, the substantially similar sequence or probe will not hybridize to the second non-complementary target sequence.

The phrases "percent identity" or "% identity" refer to the percentage of sequence similarity found in a comparison of two or more amino acid or nucleic acid sequences. Percent identity can be determined electronically, e.g., by using the MEGALIGN program (DNASTAR) which creates alignments between two or more sequences according to methods selected by the user, e.g., the clustal method. (See, e.g., Higgins, D. G. and P. M. Sharp (1988) Gene 73:237–244.) The clustal algorithm groups sequences into clusters by examining the distances between all pairs. The clusters are aligned pairwise and then in groups. The percentage similarity between two amino acid sequences, e.g., sequence A and sequence B, is calculated by dividing the length of sequence A, minus the number of gap residues in sequence A, minus the number of gap residues in sequence B, into the sum of the residue matches between sequence A and sequence B, times one hundred. Gaps of low or of no similarity between the two amino acid sequences are not included in determining percentage similarity. Percent identity between nucleic acid sequences can also be counted or calculated by other methods known in the art, e.g., the Jotun Hein method. (See, e.g., Hein, J. (1990) Methods Enzymol. 183:626–645.) Identity between sequences can also be determined by other methods known in the art, e.g., by varying hybridization conditions.

"Human artificial chromosomes" (HACs) are linear microchromosomes which may contain DNA sequences of about 6 kb to 10 Mb in size, and which contain all of the elements required for stable mitotic chromosome segregation and maintenance.

The term "humanized antibody" refers to antibody molecules in which the amino acid sequence in the non-antigen binding regions has been altered so that the antibody more closely resembles a human antibody, and still retains its original binding ability.

"Hybridization" refers to any process by which a strand of nucleic acid binds with a complementary strand through base pairing.

The term "hybridization complex" refers to a complex formed between two nucleic acid sequences by virtue of the formation of hydrogen bonds between complementary bases. A hybridization complex may be formed in solution (e.g., $C_0t$ or $R_0t$ analysis) or formed between one nucleic acid sequence present in solution and another nucleic acid sequence immobilized on a solid support (e.g., paper, membranes, filters, chips, pins or glass slides, or any other appropriate substrate to which cells or their nucleic acids have been fixed).

The words "insertion" or "addition" refer to changes in an amino acid or nucleotide sequence resulting in the addition of one or more amino acid residues or nucleotides, respectively, to the sequence found in the naturally occurring molecule.

"Immune response" can refer to conditions associated with inflammation, trauma, immune disorders, or infectious or genetic disease, etc. These conditions can be characterized by expression of various factors, e.g., cytokines, chemokines, and other signaling molecules, which may affect cellular and systemic defense systems.

The term "microarray" refers to an arrangement of distinct polynucleotides on a substrate.

The terms "element" or "array element" in a microarray context, refer to hybridizable polynucleotides arranged on the surface of a substrate.

The term "modulate" refers to a change in the activity of HUCYP. For example, modulation may cause an increase or a decrease in protein activity, binding characteristics, or any other biological, functional, or immunological properties of HUCYP.

The phrases "nucleic acid" or "nucleic acid sequence" refer to a nucleotide, oligonucleotide, polynucleotide, or any fragment thereof. These phrases also refer to DNA or RNA of genomic or synthetic origin which may be single-stranded or double-stranded and may represent the sense or the antisense strand, to peptide nucleic acid (PNA), or to any DNA-like or RNA-like material. In this context, "fragments" refers to those nucleic acid sequences which, when translated, would produce polypeptides retaining some functional characteristic, e.g., antigenicity, or structural domain characteristic, e.g., ATP-binding site, of the full-length polypeptide.

The terms "operably associated" or "operably linked" refer to functionally related nucleic acid sequences. A promoter is operably associated or operably linked with a coding sequence if the promoter controls the translation of the encoded polypeptide. While operably associated or operably linked nucleic acid sequences can be contiguous and in the same reading frame, certain genetic elements, e.g., repressor genes, are not contiguously linked to the sequence encoding the polypeptide but still bind to operator sequences that control expression of the polypeptide.

The term "oligonucleotide" refers to a nucleic acid sequence of at least about 6 nucleotides to 60 nucleotides, preferably about 15 to 30 nucleotides, and most preferably about 20 to 25 nucleotides, which can be used in PCR amplification or in a hybridization assay or microarray. "Oligonucleotide" is substantially equivalent to the terms "amplimer," "primer," "oligomer," and "probe," as these terms are commonly defined in the art.

"Peptide nucleic acid" (PNA) refers to an antisense molecule or anti-gene agent which comprises an oligonucleotide of at least about 5 nucleotides in length linked to a peptide backbone of amino acid residues ending in lysine. The terminal lysine confers solubility to the composition. PNAs preferentially bind complementary single stranded DNA or RNA and stop transcript elongation, and may be pegylated to extend their lifespan in the cell.

The term "sample" is used in its broadest sense. A sample suspected of containing nucleic acids encoding HUCYP, or fragments thereof, or HUCYP itself, may comprise a bodily fluid; an extract from a cell, chromosome, organelle, or membrane isolated from a cell; a cell; genomic DNA, RNA, or cDNA, in solution or bound to a substrate; a tissue; a tissue print; etc.

The terms "specific binding" or "specifically binding" refer to that interaction between a protein or peptide and an agonist, an antibody, or an antagonist. The interaction is dependent upon the presence of a particular structure of the protein, e.g., the antigenic determinant or epitope, recognized by the binding molecule. For example, if an antibody is specific for epitope "A," the presence of a polypeptide containing the epitope A, or the presence of free unlabeled A, in a reaction containing free labeled A and the antibody will reduce the amount of labeled A that binds to the antibody.

The term "stringent conditions" refers to conditions which permit hybridization between polynucleotides and the claimed polynucleotides. Stringent conditions can be defined by salt concentration, the concentration of organic solvent, e.g., formamide, temperature, and other conditions well known in the art. In particular, stringency can be increased by reducing the concentration of salt, increasing the concentration of formamide, or raising the hybridization temperature.

The term "substantially purified" refers to nucleic acid or amino acid sequences that are removed from their natural environment and are isolated or separated, and are at least about 60% free, preferably about 75% free, and most preferably about 90% free from other components with which they are naturally associated.

A "substitution" refers to the replacement of one or more amino acids or nucleotides by different amino acids or nucleotides, respectively.

"Substrate" refers to any suitable rigid or semi-rigid support including membranes, filters, chips, slides, wafers, fibers, magnetic or nonmagnetic beads, gels, tubing, plates, polymers, microparticles and capillaries. The substrate can have a variety of surface forms, such as wells, trenches, pins, channels and pores, to which polynucleotides or polypeptides are bound.

"Transformation" describes a process by which exogenous DNA enters and changes a recipient cell. Transformation may occur under natural or artificial conditions according to various methods well known in the art, and may rely on any known method for the insertion of foreign nucleic acid sequences into a prokaryotic or eukaryotic host cell. The method for transformation is selected based on the type of host cell being transformed and may include, but is not limited to, viral infection, electroporation, heat shock, lipofection, and particle bombardment. The term "transformed" cells includes stably transformed cells in which the inserted DNA is capable of replication either as an autonomously replicating plasmid or as part of the host chromosome, as well as transiently transformed cells which express the inserted DNA or RNA for limited periods of time.

A "variant" of HUCYP polypeptides refers to an amino acid sequence that is altered by one or more amino acid residues. The variant may have "conservative" changes, wherein a substituted amino acid has similar structural or chemical properties (e.g., replacement of leucine with isoleucine). More rarely, a variant may have "nonconservative" changes (e.g., replacement of glycine with tryptophan). Analogous minor variations may also include amino acid deletions or insertions, or both. Guidance in determining which amino acid residues may be substituted, inserted, or deleted without abolishing biological or immunological activity may be found using computer programs well known in the art, for example, LASERGENE software (DNASTAR).

The term "variant," when used in the context of a polynucleotide sequence, may encompass a polynucleotide sequence related to HUCYP. This definition may also include, for example, "allelic" (as defined above), "splice," "species," or "polymorphic" variants. A splice variant may have significant identity to a reference molecule, but will generally have a greater or lesser number of polynucleotides due to alternate splicing of exons during mRNA processing. The corresponding polypeptide may possess additional functional domains or an absence of domains. Species variants are polynucleotide sequences that vary from one species to another. The resulting polypeptides generally will have significant amino acid identity relative to each other. A polymorphic variant is a variation in the polynucleotide sequence of a particular gene between individuals of a given species. Polymorphic variants also may encompass "single nucleotide polymorphisms" (SNPs) in which the polynucleotide sequence varies by one base. The presence of SNPs may be indicative of, for example, a certain population, a disease state, or a propensity for a disease state.

The Invention

The invention is based on the discovery of a new human cytochrome P450 (HUCYP), the polynucleotides encoding HUCYP, and the use of these compositions for the diagnosis, treatment, or prevention of cell proliferative, developmental, autoimmune/inflammatory, and metabolic disorders.

Nucleic acids encoding the HUCYP of the present invention were identified in Incyte Clone 991729H1 from the colon cDNA library (COLNNOT11) using a computer search for nucleotide and/or amino acid sequence alignments. A consensus sequence, SEQ ID NO:2, was derived from the following overlapping and/or extended nucleic acid sequences: Incyte Clones 2812042H1 (OVARNOT10), 4502047H1 (BRAVTXT02), 2100169H1 (BRAITUT02), 991729R6 and 991729H1 (COLNNOT11), 038338R6 (HUVENOB01), 1996448H1 (BRSTTUT03), 687353H1 (UTRSNOT02), 1700412F6 (BLADTUT05), 4538247H1 (OVARNOT12), and 2381571F6 (ISLTNOT01).

In one embodiment, the invention encompasses a polypeptide comprising the amino acid sequence of SEQ ID NO:1, as shown in FIGS. 1A, 1B, 1C, 1D, and 1E. HUCYP is 462 amino acids in length and has three potential N-glycosylation sites at residues N94, N217, and N246; eleven potential casein kinase 2 phosphorylation sites as residues T36, S53, S116, S155, S183, T184, T293, T294, T442, S449, and S450; and seven potential protein kinase C phosphorylation sites at residues S134, T219, T281, T333, T336, S449, and S459. PFAM analysis indicates that HUCYP resembles P450 proteins from I32 through R46 1. PRINTS analysis indicates that HUCYP resembles E-class P450 Group I proteins from H62 through L81, from C285 through G311, from A367 through D391; resembles E-class P450 Group II proteins from Q265 through T293, from T294 through G311, and from T377 through E392; resembles E-class P450 Group IV proteins from E56 through V79, from L372 through D390, and from C409 through V427; resembles P450 superfamily proteins from T294 through N307; and resembles B-class P450 proteins from Q373 through R388. HUCYP shares conserved residues with cytochrome P450s in the potential heme-iron ligand region at F403, S404, G405, C409, and P410. C409 is the potential heme-binding residue. Like other eukaryotic cytochrome P450s, HUCYP contains a potentially membrane-spanning region in its first 15 to 20 residues. SPScan and HMM indicate that HUCYP has a potential signal peptide from M1 through about A18 or a potential transmembrane sequence from M1 through about Y23. A fragment of SEQ ID NO:2 from about nucleotide 109 to about nucleotide 153 is useful in hybridization or amplification technologies to identify SEQ ID NO:2 and to distinguish between SEQ ID NO:2 and a related sequence. Northern analysis shows the expression of this sequence in various libraries, 72% of which are associated with cancer and cell proliferation, 28% of which are associated with inflammation and immune response, 25% of which are reproductive tissues, 19% of which are nervous tissues, 19% of which are gastrointestinal tissues, and 16% of which are cardiovascular tissues. Of particular note is the expression of HUCYP in cancers of the liver, colon, uterus, testes, lung, breast, brain, and bladder, and in leukemia.

The invention also encompasses HUCYP variants. A preferred HUCYP variant is one which has at least about 80%, more preferably at least about 90%, and most preferably at least about 95% amino acid sequence identity to the HUCYP amino acid sequence, and which contains at least one functional or structural characteristic of HUCYP.

The invention also encompasses polynucleotides which encode HUCYP. In a particular embodiment, the invention encompasses a polynucleotide sequence comprising the sequence of SEQ ID NO:2, which encodes HUCYP.

The invention also encompasses a variant of a polynucleotide sequence encoding HUCYP. In particular, such a variant polynucleotide sequence will have at least about 70%, more preferably at least about 85%, and most preferably at least about 95% polynucleotide sequence identity to the polynucleotide sequence encoding HUCYP. A particular aspect of the invention encompasses a variant of SEQ ID NO:2 which has at least about 70%, more preferably at least about 85%, and most preferably at least about 95% polynucleotide sequence identity to SEQ ID NO:2. Any one of the polynucleotide variants described above can encode an amino acid sequence which contains at least one functional or structural characteristic of HUCYP.

It will be appreciated by those skilled in the art that as a result of the degeneracy of the genetic code, a multitude of polynucleotide sequences encoding HUCYP, some bearing minimal similarity to the polynucleotide sequences of any known and naturally occurring gene, may be produced. Thus, the invention contemplates each and every possible variation of polynucleotide sequence that could be made by selecting combinations based on possible codon choices. These combinations are made in accordance with the standard triplet genetic code as applied to the polynucleotide sequence of naturally occurring HUCYP, and all such variations are to be considered as being specifically disclosed.

Although nucleotide sequences which encode HUCYP and its variants are preferably capable of hybridizing to the nucleotide sequence of the naturally occurring HUCYP under appropriately selected conditions of stringency, it may be advantageous to produce nucleotide sequences encoding HUCYP or its derivatives possessing a substantially different codon usage, e.g., inclusion of non-naturally occurring codons. Codons may be selected to increase the rate at which expression of the peptide occurs in a particular prokaryotic or eukaryotic host in accordance with the frequency with which particular codons are utilized by the host. Other reasons for substantially altering the nucleotide sequence encoding HUCYP and its derivatives without altering the encoded amino acid sequences include the production of RNA transcripts having more desirable properties, such as a greater half-life, than transcripts produced from the naturally occurring sequence.

The invention also encompasses production of DNA sequences which encode HUCYP and HUCYP derivatives, or fragments thereof, entirely by synthetic chemistry. After production, the synthetic sequence may be inserted into any of the many available expression vectors and cell systems using reagents well known in the art. Moreover, synthetic chemistry may be used to introduce mutations into a sequence encoding HUCYP or any fragment thereof.

Also encompassed by the invention are polynucleotide sequences that are capable of hybridizing to the claimed polynucleotide sequences, and, in particular, to those shown in SEQ ID NO:2, or to a fragment of SEQ ID NO:2, under various conditions of stringency. (See, e.g., Wahl, G. M. and S. L. Berger (1987) Methods Enzymol. 152:399–407; Kimmel, A. R. (1987) Methods Enzymol. 152:507–511.) For example, stringent salt concentration will ordinarily be less than about 750 mM NaCl and 75 mM trisodium citrate, preferably less than about 500 mM NaCl and 50 mM trisodium citrate, and most preferably less than about 250 mM NaCl and 25 mM trisodium citrate. Low stringency hybridization can be obtained in the absence of organic solvent, e.g., formamide, while high stringency hybridization can be obtained in the presence of at least about 35% formamide, and most preferably at least about 50% formamide. Stringent temperature conditions will ordinarily include temperatures of at least about 30° C., more preferably of at least about 37° C., and most preferably of at least about 42° C. Varying additional parameters, such as hybridization time, the concentration of detergent, e.g., sodium dodecyl sulfate (SDS), and the inclusion or exclusion of carrier DNA, are well known to those skilled in the art. Various levels of stringency are accomplished by combining these various conditions as needed. In a preferred embodiment, hybridization will occur at 30° C. in 750 mM NaCl, 75 mM trisodium citrate, and 1% SDS. In a more preferred embodiment, hybridization will occur at 37° C. in 500 mM NaCl, 50 mM trisodium citrate, 1% SDS, 35% formamide, and 100 µg/ml denatured salmon sperm DNA (ssDNA). In a most preferred embodiment, hybridization will occur at 42° C. in 250 mM NaCl, 25 mM trisodium citrate, 1% SDS, 50% formamide, and 200 μg/ml ssDNA. Useful variations on these conditions will be readily apparent to those skilled in the art.

The washing steps which follow hybridization can also vary in stringency. Wash stringency conditions can be defined by salt concentration and by temperature. As above, wash stringency can be increased by decreasing salt concentration or by increasing temperature. For example, stringent salt concentration for the wash steps will preferably be less than about 30 mM NaCl and 3 mM trisodium citrate, and most preferably less than about 15 mM NaCl and 1.5 mM trisodium citrate. Stringent temperature conditions for the wash steps will ordinarily include temperature of at least about 25° C., more preferably of at least about 42° C., and most preferably of at least about 68° C. In a preferred embodiment, wash steps will occur at 25° C. in 30 mM NaCl, 3 mM trisodium citrate, and 0.1% SDS. In a more preferred embodiment, wash steps will occur at 42° C. in 15 mM NaCl, 1.5 mM trisodium citrate, and 0.1% SDS. In a most preferred embodiment, wash steps will occur at 68° C. in 15 mM NaCl, 1.5 mM trisodium citrate, and 0.1% SDS. Additional variations on these conditions will be readily apparent to those skilled in the art.

Methods for DNA sequencing are well known in the art and may be used to practice any of the embodiments of the invention. The methods may employ such enzymes as the Klenow fragment of DNA polymerase I, SEQUENASE (US Biochemical, Cleveland Ohio), Taq polymerase (Perkin-Elmer), thermostable T7 polymerase (Amersham Pharmacia Biotech, Piscataway N.J.), or combinations of polymerases and proofreading exonucleases such as those found in the ELONGASE amplification system (Life Technologies, Gaithersburg Md.). Preferably, sequence preparation is automated with machines such as the Robbins Hydra microdispenser (Robbins Scientific, Sunnyvale Calif.), Hamilton MICROLAB 2200 (Hamilton, Reno Nev.), Peltier Thermal Cycler 200 (PTC200; M J Research, Watertown Mass.) and the ABI CATALYST 800 (Perkin-Elmer). Sequencing is then carried out using the ABI 373 or 377 DNA sequencing systems (Perkin-Elmer), the MEGABACE 1000 DNA sequencing system (Molecular Dynamics, Sunnyvale Calif.), or other systems known in the art. The resulting sequences are analyzed using a variety of algorithms which are well known in the art. (See, e.g., Ausubel, F. M. (1997) *Short Protocols in Molecular Biology*, John Wiley & Sons, New York N.Y., unit 7.7; Meyers, R. A. (1995) *Molecular Biology and Biotechnology*, Wiley VCH, New York N.Y., pp. 856–853.)

The nucleic acid sequences encoding HUCYP may be extended utilizing a partial nucleotide sequence and employing various PCR-based methods known in the art to detect upstream sequences, such as promoters and regulatory elements. For example, one method which may be employed, restriction-site PCR, uses universal and nested primers to amplify unknown sequence from genomic DNA within a cloning vector. (See, e.g., Sarkar, G. (1993) PCR Methods Applic. 2:318–322.) Another method, inverse PCR, uses primers that extend in divergent directions to amplify unknown sequence from a circularized template. The template is derived from restriction fragments comprising a known genomic locus and surrounding sequences. (See, e.g., Triglia, T. et al. (1988) Nucleic Acids Res. 16:8186.) A third method, capture PCR, involves PCR amplification of DNA fragments adjacent to known sequences in human and yeast artificial chromosome DNA. (See, e.g., Lagerstrom, M. et al. (1991) PCR Methods Applic. 1:111–119.) In this method, multiple restriction enzyme digestions and ligations may be used to insert an engineered double-stranded sequence into a region of unknown sequence before performing PCR. Other methods which may be used to retrieve unknown sequences are known in the art. (See, e.g., Parker, J. D. et al. (1991) Nucleic Acids Res. 19:3055–306). Additionally, one may use PCR, nested primers, and PROMOTERFINDER libraries (Clontech, Palo Alto Calif.) to walk genomic DNA. This procedure avoids the need to screen libraries and is useful in finding intron/exon junctions. For all PCR-based methods, primers may be designed using commercially available software, such as OLIGO 4.06 primer analysis software (National Biosciences, Plymouth Minn.) or another appropriate program, to be about 22 to 30 nucleotides in length, to have a GC content of about 50% or more, and to anneal to the template at temperatures of about 68° C. to 72° C.

When screening for full-length cDNAs, it is preferable to use libraries that have been size-selected to include larger cDNAs. In addition, random-primed libraries, which often include sequences containing the 5' regions of genes, are preferable for situations in which an oligo d(T) library does not yield a full-length cDNA. Genomic libraries may be useful for extension of sequence into 5' non-transcribed regulatory regions.

Capillary electrophoresis systems which are commercially available may be used to analyze the size or confirm the nucleotide sequence of sequencing or PCR products. In particular, capillary sequencing may employ flowable polymers for electrophoretic separation, four different nucleotide-specific, laser-stimulated fluorescent dyes, and a charge coupled device camera for detection of the emitted wavelengths. Output/light intensity may be converted to electrical signal using appropriate software (e.g., GENOTYPER and SEQUENCE NAVIGATOR, Perkin-Elmer), and the entire process from loading of samples to computer analysis and electronic data display may be computer controlled. Capillary electrophoresis is especially preferable for sequencing small DNA fragments which may be present in limited amounts in a particular sample.

In another embodiment of the invention, polynucleotide sequences or fragments thereof which encode HUCYP may be cloned in recombinant DNA molecules that direct expression of HUCYP, or fragments or functional equivalents thereof, in appropriate host cells. Due to the inherent degeneracy of the genetic code, other DNA sequences which encode substantially the same or a functionally equivalent amino acid sequence may be produced and used to express HUCYP.

The nucleotide sequences of the present invention can be engineered using methods generally known in the art in order to alter HUCYP-encoding sequences for a variety of purposes including, but not limited to, modification of the cloning, processing, and/or expression of the gene product. DNA shuffling by random fragmentation and PCR reassembly of gene fragments and synthetic oligonucleotides may be used to engineer the nucleotide sequences. For example, oligonucleotide-mediated site-directed mutagenesis may be used to introduce mutations that create new restriction sites, alter glycosylation patterns, change codon preference, produce splice variants, and so forth.

In another embodiment, sequences encoding HUCYP may be synthesized, in whole or in part, using chemical methods well known in the art. (See, e.g., Caruthers, M. H. et al. (1980) Nucl. Acids Res. Symp. Ser. (7):215–223, and Horn, T. et al. (1980) Nucl. Acids Symp. Ser. (7):225–232.) Alternatively, HUCYP itself or a fragment thereof may be synthesized using chemical methods. For example, peptide synthesis can be performed using various solid-phase techniques. (See, e.g., Roberge, J. Y. et al. (1995) Science 269:202–204.) Automated synthesis may be achieved using the ABI 431A peptide synthesizer (Perkin-Elmer). Additionally, the amino acid sequence of HUCYP, or any part thereof, may be altered during direct synthesis and/or combined with sequences from other proteins, or any part thereof, to produce a variant polypeptide.

The peptide may be substantially purified by preparative high performance liquid chromatography. (See, e.g, Chiez, R. M. and F. Z. Regnier (1990) Methods Enzymol. 182:392–421.) The composition of the synthetic peptides may be confirmed by amino acid analysis or by sequencing. (See, e.g., Creighton, T. (1984) *Proteins. Structures and Molecular Properties*, W H Freeman, New York N.Y.)

In order to express a biologically active HUCYP, the nucleotide sequences encoding HUCYP or derivatives thereof may be inserted into an appropriate expression vector, i.e., a vector which contains the necessary elements for transcriptional and translational control of the inserted coding sequence in a suitable host. These elements include regulatory sequences, such as enhancers, constitutive and inducible promoters, and 5' and 3' untranslated regions in the vector and in polynucleotide sequences encoding HUCYP. Such elements may vary in their strength and specificity. Specific initiation signals may also be used to achieve more efficient translation of sequences encoding HUCYP. Such signals include the ATG initiation codon and adjacent sequences, e.g. the Kozak sequence. In cases where sequences encoding HUCYP and its initiation codon and upstream regulatory sequences are inserted into the appropriate expression vector, no additional transcriptional or translational control signals may be needed. However, in cases where only coding sequence, or a fragment thereof, is inserted, exogenous translational control signals including an in-frame ATG initiation codon should be provided by the vector. Exogenous translational elements and initiation codons may be of various origins, both natural and synthetic. The efficiency of expression may be enhanced by the inclusion of enhancers appropriate for the particular host cell system used. (See, e.g., Scharf, D. et al. (1994) Results Probl. Cell Differ. 20:125–162.)

Methods which are well known to those skilled in the art may be used to construct expression vectors containing sequences encoding HUCYP and appropriate transcriptional and translational control elements. These methods include in vitro recombinant DNA techniques, synthetic techniques, and in vivo genetic recombination. (See, e.g., Sambrook, J. et al. (1989) *Molecular Cloning. A Laboratory Manual*, Cold Spring Harbor Press, Plainview N.Y., ch. 4, 8, and 16–17; Ausubel, F. M. et al. (1995) *Current Protocols in Molecular Biology*, John Wiley & Sons, New York N.Y., ch. 9, 13, and 16.)

A variety of expression vector/host systems may be utilized to contain and express sequences encoding HUCYP. These include, but are not limited to, microorganisms such as bacteria transformed with recombinant bacteriophage, plasmid, or cosmid DNA expression vectors; yeast transformed with yeast expression vectors; insect cell systems infected with viral expression vectors (e.g., baculovirus); plant cell systems transformed with viral expression vectors (e.g., cauliflower mosaic virus, CaMV, or tobacco mosaic virus, TMV) or with bacterial expression vectors (e.g., Ti or pBR322 plasmids); or animal cell systems. The invention is not limited by the host cell employed.

In bacterial systems, a number of cloning and expression vectors may be selected depending upon the use intended for polynucleotide sequences encoding HUCYP. For example, routine cloning, subcloning, and propagation of polynucleotide sequences encoding HUCYP can be achieved using a multifunctional *E. coli* vector such as PBLUESCRIPT (Stratagene, La Jolla Calif.) or pSPORT1 plasmid (Life Technologies). Ligation of sequences encoding HUCYP into the vector's multiple cloning site disrupts the lacZ gene, allowing a colorimetric screening procedure for identification of transformed bacteria containing recombinant molecules. In addition, these vectors may be useful for in vitro transcription, dideoxy sequencing, single strand rescue with helper phage, and creation of nested deletions in the cloned sequence. (See, e.g., Van Heeke, G. and S. M. Schuster (1989) J. Biol. Chem. 264:5503–5509.) When large quantities of HUCYP are needed, e.g. for the production of antibodies, vectors which direct high level expression of HUCYP may be used. For example, vectors containing the strong, inducible T5 or T7 bacteriophage promoter may be used.

Yeast expression systems may be used for production of HUCYP. A number of vectors containing constitutive or inducible promoters, such as alpha factor, alcohol oxidase, and PGH promoters, may be used in the yeast *Saccharomyces cerevisiae* or *Pichia pastoris*. In addition, such vectors direct either the secretion or intracellular retention of expressed proteins and enable integration of foreign sequences into the host genome for stable propagation. (See, e.g., Ausubel, 1995, supra; Grant et al. (1987) Methods Enzymol. 153:516–54; and Scorer, C. A. et al. (1994) Bio/Technology 12:181–184.)

Plant systems may also be used for expression of HUCYP. Transcription of sequences encoding HUCYP may be driven by viral promoters, e.g., the 35S and 19S promoters of CaMV used alone or in combination with the omega leader sequence from TMV (Takamatsu, N. (1987) EMBO J. 6:307–311). Alternatively, plant promoters such as the small subunit of RUBISCO or heat shock promoters may be used. (See, e.g., Coruzzi, G. et al. (1984) EMBO J. 3:1671–1680; Broglie, R. et al. (1984) Science 224:838–843; and Winter, J. et al. (1991) Results Probl. Cell Differ. 17:85–105.) These constructs can be introduced into plant cells by direct DNA transformation or pathogen-mediated transfection. (See, e.g., *The McGraw Hill Yearbook of Science and Technology* (1992) McGraw Hill, New York N.Y., pp. 191–196.)

In mammalian cells, a number of viral-based expression systems may be utilized. In cases where an adenovirus is used as an expression vector, sequences encoding HUCYP may be ligated into an adenovirus transcription/translation complex consisting of the late promoter and tripartite leader sequence. Insertion in a non-essential E1 or E3 region of the viral genome may be used to obtain infective virus which expresses HUCYP in host cells. (See, e.g., Logan, J. and T. Shenk (1984) Proc. Natl. Acad. Sci. 81:3655–3659.) In addition, transcription enhancers, such as the Rous sarcoma virus (RSV) enhancer, may be used to increase expression in mammalian host cells. SV40 or EBV-based vectors may also be used for high-level protein expression.

Human artificial chromosomes (HACs) may also be employed to deliver larger fragments of DNA than can be contained in and expressed from a plasmid. HACs of about 6 kb to 10 Mb are constructed and delivered via conventional delivery methods (liposomes, polycationic amino polymers, or vesicles) for therapeutic purposes. (See, e.g., Harrington, J. J. et al. (1997) Nat Genet. 15:345–355.)

For long term production of recombinant proteins in mammalian systems, stable expression of HUCYP in cell lines is preferred. For example, sequences encoding HUCYP can be transformed into cell lines using expression vectors which may contain viral origins of replication and/or endogenous expression elements and a selectable marker gene on the same or on a separate vector. Following the introduction of the vector, cells may be allowed to grow for about 1 to 2 days in enriched media before being switched to selective media. The purpose of the selectable marker is to confer resistance to a selective agent, and its presence allows growth and recovery of cells which successfully express the introduced sequences. Resistant clones of stably transformed cells may be propagated using tissue culture techniques appropriate to the cell type.

Any number of selection systems may be used to recover transformed cell lines. These include, but are not limited to, the herpes simplex virus thymidine kinase and adenine phosphoribosyltransferase genes, for use in tk⁻ or apr⁻ cells, respectively. (See, e.g., Wigler, M. et al. (1977) Cell 11:223–232; Lowy, I. et al. (1980) Cell 22:817–823.) Also, antimetabolite, antibiotic, or herbicide resistance can be used as the basis for selection. For example, dhfr confers resistance to methotrexate; neo confers resistance to the aminoglycosides, neomycin and G-418; and als or pat confer resistance to chlorsulfuron and phosphinotricin acetyltransferase, respectively. (See, e.g., Wigler, M. et al. (1980) Proc. Natl. Acad. Sci. 77:3567–3570; Colbere-Garapin, F. et al. (1981) J. Mol. Biol. 150:1–14.) Additional selectable genes have been described, e.g., trpB and hisD, which alter cellular requirements for metabolites. (See, e.g., Hartman, S. C. and R. C. Mulligan (1988) Proc. Natl. Acad. Sci. 85:8047–8051.) Visible markers, e.g., anthocyanins, green fluorescent proteins (GFP; Clontech), β glucuronidase and its substrate β-glucuronide, or luciferase and its substrate luciferin may be used. These markers can be used not only to identify transformants, but also to quantify the amount of transient or stable protein expression attributable to a specific vector system. (See, e.g., Rhodes, C. A. (1995) Methods Mol. Biol. 55:121–131.)

Although the presence/absence of marker gene expression suggests that the gene of interest is also present, the presence and expression of the gene may need to be confirmed. For example, if the sequence encoding HUCYP is inserted within a marker gene sequence, transformed cells containing sequences encoding HUCYP can be identified by the absence of marker gene function. Alternatively, a marker gene can be placed in tandem with a sequence encoding HUCYP under the control of a single promoter. Expression of the marker gene in response to induction or selection usually indicates expression of the tandem gene as well.

In general, host cells that contain the nucleic acid sequence encoding HUCYP and that express HUCYP may be identified by a variety of procedures known to those of skill in the art. These procedures include, but are not limited to, DNA—DNA or DNA—RNA hybridizations, PCR amplification, and protein bioassay or immunoassay techniques which include membrane, solution, or chip based technologies for the detection and/or quantification of nucleic acid or protein sequences.

Immunological methods for detecting and measuring the expression of HUCYP using either specific polyclonal or monoclonal antibodies are known in the art. Examples of such techniques include enzyme-linked immunosorbent assays (ELISAs), radioimmunoassays (RIAs), and fluorescence activated cell sorting (FACS). A two-site, monoclonal-based immunoassay utilizing monoclonal antibodies reactive to two non-interfering epitopes on HUCYP is preferred, but a competitive binding assay may be employed. These and other assays are well known in the art. (See, e.g., Hampton, R. et al. (1990) Serological Methods, a Laboratory Manual, APS Press, St Paul Minn., Sect. IV; Coligan, J. E. et al. (1997) Current Protocols in Immunology, Greene Pub. Associates and Wiley-Interscience, New York N.Y.; and Pound, J. D. (1998) Immunochemical Protocols, Humana Press, Totowa N.J.).

A wide variety of labels and conjugation techniques are known by those skilled in the art and may be used in various nucleic acid and amino acid assays. Means for producing labeled hybridization or PCR probes for detecting sequences related to polynucleotides encoding HUCYP include oligolabeling, nick translation, end-labeling, or PCR amplification using a labeled nucleotide. Alternatively, the sequences encoding HUCYP, or any fragments thereof, may be cloned into a vector for the production of an mRNA probe. Such vectors are known in the art, are commercially available, and may be used to synthesize RNA probes in vitro by addition of an appropriate RNA polymerase such as T7, T3, or SP6 and labeled nucleotides. These procedures may be conducted using a variety of commercially available kits, such as those provided by Amersham Pharmacia Biotech, Promega (Madison Wis.), and US Biochemical. Suitable reporter molecules or labels which may be used for ease of detection include radionuclides, enzymes, fluorescent, chemiluminescent, or chromogenic agents, as well as substrates, cofactors, inhibitors, magnetic particles, and the like.

Host cells transformed with nucleotide sequences encoding HUCYP may be cultured under conditions suitable for the expression and recovery of the protein from cell culture. The protein produced by a transformed cell may be secreted or retained intracellularly depending on the sequence and/or the vector used. As will be understood by those of skill in the art, expression vectors containing polynucleotides which encode HUCYP may be designed to contain signal sequences which direct secretion of HUCYP through a prokaryotic or eukaryotic cell membrane.

In addition, a host cell strain may be chosen for its ability to modulate expression of the inserted sequences or to process the expressed protein in the desired fashion. Such modifications of the polypeptide include, but are not limited to, acetylation, carboxylation, glycosylation, phosphorylation, lipidation, and acylation. Post-translational processing which cleaves a "prepro" form of the protein may also be used to specify protein targeting, folding, and/or activity. Different host cells which have specific cellular machinery and characteristic mechanisms for post-translational activities (e.g., CHO, HeLa, MDCK, HEK293, and WI38), are available from the American Type Culture Collection (ATCC, Bethesda Md.) and may be chosen to ensure the correct modification and processing of the foreign protein.

In another embodiment of the invention, natural, modified, or recombinant nucleic acid sequences encoding HUCYP may be ligated to a heterologous sequence resulting in translation of a fusion protein in any of the aforementioned host systems. For example, a chimeric HUCYP protein containing a heterologous moiety that can be recognized by a commercially available antibody may facilitate the screening of peptide libraries for inhibitors of HUCYP activity. Heterologous protein and peptide moieties may also facilitate purification of fusion proteins using commercially available affinity matrices. Such moieties include, but are not limited to, glutathione S-transferase (GST), maltose binding protein (MBP), thioredoxin (Trx), calmodulin binding peptide (CBP), 6-His, FLAG, c-myc, and hemagglutinin (HA). GST, MBP, Trx, CBP, and 6-His enable purification of their cognate fusion proteins on immobilized glutathione, maltose, phenylarsine oxide, calmodulin, and metal-chelate resins, respectively. FLAG, c-myc, and hemagglutinin (HA) enable immunoaffinity purification of fusion proteins using commercially available monoclonal and polyclonal antibodies that specifically recognize these epitope tags. A fusion protein may also be engineered to contain a proteolytic cleavage site located between the HUCYP encoding sequence and the heterologous protein sequence, so that HUCYP may be cleaved away from the heterologous moiety following purification. Methods for fusion protein expression and purification are discussed in Ausubel (1995, supra, ch 10). A variety of commercially available kits may also be used to facilitate expression and purification of fusion proteins.

In a further embodiment of the invention, synthesis of radiolabeled HUCYP may be achieved in vitro using the TNT rabbit reticulocyte lysate or wheat germ extract systems (Promega). These systems couple transcription and translation of protein-coding sequences operably associated with the T7, T3, or SP6 promoters. Translation takes place in the presence of a radiolabeled amino acid precursor, preferably $^{35}$S-methionine.

Fragments of HUCYP may be produced not only by recombinant production, but also by direct peptide synthesis using solid-phase techniques. (See, e.g., Creighton, supra pp. 55–60.) Protein synthesis may be performed by manual techniques or by automation. Automated synthesis may be achieved, for example, using the ABI 431A peptide synthesizer (Perkin-Elmer). Various fragments of HUCYP may be synthesized separately and then combined to produce the full length molecule.

Therapeutics

Chemical and structural similarity, e.g., in the context of sequences and motifs, exists between regions of HUCYP and cytochrome P450 proteins. In addition, the expression of HUCYP is closely associated with cancer and cell proliferation, inflammation and immune response, reproductive tissues, nervous tissues, gastrointestinal tissues, and cardiovascular tissues. Therefore, HUCYP appears to play a role in cell proliferative, developmental, autoimmune/inflammatory, and metabolic disorders. In the treatment of disorders associated with increased HUCYP expression or activity, it is desirable to decrease the expression or activity of HUCYP. In the treatment of disorders associated with decreased HUCYP expression or activity, it is desirable to increase the expression or activity of HUCYP.

Therefore, in one embodiment, HUCYP or a fragment or derivative thereof may be administered to a subject to treat or prevent a disorder associated with decreased expression or activity of HUCYP. Examples of such disorders include, but are not limited to, a cell proliferative disorder such as actinic keratosis, arteriosclerosis, atherosclerosis, bursitis, cirrhosis, hepatitis, mixed connective tissue disease (MCTD), myelofibrosis, paroxysmal nocturnal hemoglobinuria, polycythemia vera, psoriasis, primary thrombocythemia, and cancers including adenocarcinoma, leukemia, lymphoma, melanoma, myeloma, sarcoma, teratocarcinoma, and, in particular, cancers of the adrenal gland, bladder, bone, bone marrow, brain, breast, cervix, gall bladder, ganglia, gastrointestinal tract, heart, kidney, liver, lung, muscle, ovary, pancreas, parathyroid, penis, prostate, salivary glands, skin, spleen, testis, thymus, thyroid, and uterus; a developmental disorder such as renal tubular acidosis, anemia, Cushing's syndrome, achondroplastic dwarfism, Duchenne and Becker muscular dystrophy, epilepsy, gonadal dysgenesis, WAGR syndrome (Wilms' tumor, aniridia, genitourinary abnormalities, and mental retardation), Smith-Magenis syndrome, myelodysplastic syndrome, hereditary mucoepithelial dysplasia, hereditary keratodermas, hereditary neuropathies such as Charcot-Marie-Tooth disease and neurofibromatosis, hypothyroidism, hydrocephalus, seizure disorders such as Syndenham's chorea and cerebral palsy, spina bifida, anencephaly, craniorachischisis, congenital glaucoma, cataract, and sensorineural hearing loss; an autoimmune/inflammatory disorder such as acquired immunodeficiency syndrome (AIDS), Addison's disease, adult respiratory distress syndrome, allergies, ankylosing spondylitis, amyloidosis, anemia, asthma, atherosclerosis, autoimmune hemolytic anemia, autoimmune thyroiditis, autoimmune polyenodocrinopathy-candidiasis-ectodermal dystrophy (APECED), bronchitis, cholecystitis, contact dermatitis, Crohn's disease, atopic dermatitis, dermatomyositis, diabetes mellitus, emphysema, episodic lymphopenia with lymphocytotoxins, erythroblastosis fetalis, erythema nodosum, atrophic gastritis, glomerulonephritis, Goodpasture's syndrome, gout, Graves' disease, Hashimoto's thyroiditis, hypereosinophilia, irritable bowel syndrome, multiple sclerosis, myasthenia gravis, myocardial or pericardial inflammation, osteoarthritis, osteoporosis, pancreatitis, polymyositis, psoriasis, Reiter's syndrome, rheumatoid arthritis, scleroderma, Sjögren's syndrome, systemic anaphylaxis, systemic lupus erythematosus, systemic sclerosis, thrombocytopenic purpura, ulcerative colitis, uveitis, Werner syndrome, complications of cancer, hemodialysis, and extracorporeal circulation, viral, bacterial, fungal, parasitic, protozoal, and helminthic infections, and trauma; and a metabolic disorder such as Addison's disease, cystic fibrosis, diabetes, fatty hepatocirrhosis, galactosemia, goiter, hyperadrenalism, hypoadrenalism, hyperparathyroidism, hypoparathyroidism, hypercholesterolemia, hyperthyroidism, hypothyroidism hyperlipidemia, hyperlipemia, lipid myopathies, obesity, lipodystrophies, and phenylketonuria, congenital adrenal hyperplasia, pseudovitamin D-deficiency rickets, cerebrotendinous xanthomatosis, and coumarin resistance.

In another embodiment, a vector capable of expressing HUCYP or a fragment or derivative thereof may be administered to a subject to treat or prevent a disorder associated with decreased expression or activity of HUCYP including, but not limited to, those described above.

In a further embodiment, a pharmaceutical composition comprising a substantially purified HUCYP in conjunction with a suitable pharmaceutical carrier may be administered to a subject to treat or prevent a disorder associated with decreased expression or activity of HUCYP including, but not limited to, those provided above.

In still another embodiment, an agonist which modulates the activity of HUCYP may be administered to a subject to treat or prevent a disorder associated with decreased expression or activity of HUCYP including, but not limited to, those listed above.

In a further embodiment, an antagonist of HUCYP may be administered to a subject to treat or prevent a disorder associated with increased expression or activity of HUCYP. Such disorders may include, but are not limited to, cell proliferative, developmental, autoimmune/inflammatory, and metabolic disorders as listed above. In one aspect, an antibody which specifically binds HUCYP may be used directly as an antagonist or indirectly as a targeting or delivery mechanism for bringing a pharmaceutical agent to cells or tissue which express HUCYP.

In an additional embodiment, a vector expressing the complement of the polynucleotide encoding HUCYP may be administered to a subject to treat or prevent a disorder associated with increased expression or activity of HUCYP including, but not limited to, those described above.

In other embodiments, any of the proteins, antagonists, antibodies, agonists, complementary sequences, or vectors of the invention may be administered in combination with other appropriate therapeutic agents. Selection of the appropriate agents for use in combination therapy may be made by one of ordinary skill in the art, according to conventional pharmaceutical principles. The combination of therapeutic agents may act synergistically to effect the treatment or prevention of the various disorders described above. Using this approach, one may be able to achieve therapeutic efficacy with lower dosages of each agent, thus reducing the potential for adverse side effects.

An antagonist of HUCYP may be produced using methods which are generally known in the art. In particular, purified HUCYP may be used to produce antibodies or to screen libraries of pharmaceutical agents to identify those which specifically bind HUCYP. Antibodies to HUCYP may also be generated using methods that are well known in the art. Such antibodies may include, but are not limited to, polyclonal, monoclonal, chimeric, and single chain antibodies, Fab fragments, and fragments produced by a Fab expression library. Neutralizing antibodies (i.e., those which inhibit dimer formation) are especially preferred for therapeutic use.

For the production of antibodies, various hosts including goats, rabbits, rats, mice, humans, and others may be immunized by injection with HUCYP or with any fragment or oligopeptide thereof which has immunogenic properties. Depending on the host species, various adjuvants may be used to increase immunological response. Such adjuvants include, but are not limited to, Freund's, mineral gels such as aluminum hydroxide, and surface active substances such as lysolecithin, pluronic polyols, polyanions, peptides, oil emulsions, KLH, and dinitrophenol. Among adjuvants used in humans, BCG (bacilli Calmette-Guerin) and *Corynebacterium parvum* are especially preferable.

It is preferred that the oligopeptides, peptides, or fragments used to induce antibodies to HUCYP have an amino acid sequence consisting of at least about 5 amino acids, and, more preferably, of at least about 10 amino acids. It is also preferable that these oligopeptides, peptides, or fragments are identical to a portion of the amino acid sequence of the natural protein and contain the entire amino acid sequence of a small, naturally occurring molecule. Short stretches of HUCYP amino acids may be fused with those of another protein, such as KLH, and antibodies to the chimeric molecule may be produced.

Monoclonal antibodies to HUCYP may be prepared using any technique which provides for the production of antibody molecules by continuous cell lines in culture. These include, but are not limited to, the hybridoma technique, the human B-cell hybridoma technique, and the EBV-hybridoma technique. (See, e.g., Kohler, G. et al. (1975) Nature 256:495–497; Kozbor, D. et al. (1985) J. Immunol. Methods 81:31–42; Cote, R. J. et al. (1983) Proc. Natl. Acad. Sci. 80:2026–2030; and Cole, S. P. et al. (1984) Mol. Cell Biol. 62:109–120.)

In addition, techniques developed for the production of "chimeric antibodies," such as the splicing of mouse antibody genes to human antibody genes to obtain a molecule with appropriate antigen specificity and biological activity, can be used. (See, e.g., Morrison, S. L. et al. (1984) Proc. Natl. Acad. Sci. 81:6851–6855; Neuberger, M. S. et al. (1984) Nature 312:604–608; and Takeda, S. et al. (1985) Nature 314:452–454.) Alternatively, techniques described for the production of single chain antibodies may be adapted, using methods known in the art, to produce HUCYP-specific single chain antibodies. Antibodies with related specificity, but of distinct idiotypic composition, may be generated by chain shuffling from random combinatorial immunoglobulin libraries. (See, e.g., Burton D. R. (1991) Proc. Natl. Acad. Sci. 88:10134–10137.)

Antibodies may also be produced by inducing in vivo production in the lymphocyte population or by screening immunoglobulin libraries or panels of highly specific binding reagents as disclosed in the literature. (See, e.g., Orlandi, R. et al. (1989) Proc. Natl. Acad. Sci. 86:3833–3837; Winter, G. et al. (1991) Nature 349:293–299.)

Antibody fragments which contain specific binding sites for HUCYP may also be generated. For example, such fragments include, but are not limited to, F(ab')2 fragments produced by pepsin digestion of the antibody molecule and Fab fragments generated by reducing the disulfide bridges of the F(ab')2 fragments. Alternatively, Fab expression libraries may be constructed to allow rapid and easy identification of monoclonal Fab fragments with the desired specificity. (See, e.g., Huse, W. D. et al. (1989) Science 246:1275–1281.)

Various immunoassays may be used for screening to identify antibodies having the desired specificity. Numerous protocols for competitive binding or immunoradiometric assays using either polyclonal or monoclonal antibodies with established specificities are well known in the art. Such immunoassays typically involve the measurement of complex formation between HUCYP and its specific antibody. A two-site, monoclonal-based immunoassay utilizing monoclonal antibodies reactive to two non-interfering HUCYP epitopes is preferred, but a competitive binding assay may also be employed (Pound, supra).

Various methods such as Scatchard analysis in conjunction with radioimmunoassay techniques may be used to assess the affinity of antibodies for HUCYP. Affinity is expressed as an association constant, $K_a$, which is defined as the molar concentration of HUCYP-antibody complex divided by the molar concentrations of free antigen and free antibody under equilibrium conditions. The $K_a$ determined for a preparation of polyclonal antibodies, which are heterogeneous in their affinities for multiple HUCYP epitopes, represents the average affinity, or avidity, of the antibodies for HUCYP. The $K_a$ determined for a preparation of monoclonal antibodies, which are monospecific for a particular HUCYP epitope, represents a true measure of affinity. High-affinity antibody preparations with $K_a$ ranging from about $10^9$ to $10^{12}$ l/mole are preferred for use in immunoassays in which the HUCYP-antibody complex must withstand rigorous manipulations. Low-affinity antibody preparations with $K_a$ ranging from about $10^6$ to $10^7$ l/mole are preferred for use in immunopurification and similar procedures which ultimately require dissociation of HUCYP, preferably in active form, from the antibody (Catty, D. (1988) *Antibodies, Volume I: A Practical Approach*, IRL Press, Washington D.C.; Liddell, J. E. and Cryer, A. (1991) *A Practical Guide to Monoclonal Antibodies*, John Wiley & Sons, New York N.Y.).

The titer and avidity of polyclonal antibody preparations may be further evaluated to determine the quality and suitability of such preparations for certain downstream applications. For example, a polyclonal antibody preparation containing at least 1–2 mg specific antibody/ml, preferably 5–10 mg specific antibody/ml, is preferred for use in procedures requiring precipitation of HUCYP-antibody complexes. Procedures for evaluating antibody specificity, titer, and avidity, and guidelines for antibody quality and usage in various applications, are generally available. (See, e.g., Catty, supra, and Coligan et al. supra.)

In another embodiment of the invention, the polynucleotides encoding HUCYP, or any fragment or complement thereof, may be used for therapeutic purposes. In one aspect, the complement of the polynucleotide encoding HUCYP may be used in situations in which it would be desirable to block the transcription of the mRNA. In particular, cells may be transformed with sequences complementary to polynucleotides encoding HUCYP. Thus, complementary molecules or fragments may be used to modulate HUCYP activity, or to achieve regulation of gene function. Such technology is now well known in the art, and sense or antisense oligonucleotides or larger fragments can be designed from various locations along the coding or control regions of sequences encoding HUCYP.

Expression vectors derived from retroviruses, adenoviruses, or herpes or vaccinia viruses, or from various bacterial plasmids, may be used for delivery of nucleotide sequences to the targeted organ, tissue, or cell population. Methods which are well known to those skilled in the art can be used to construct vectors to express nucleic acid sequences complementary to the polynucleotides encoding HUCYP. (See, e.g., Sambrook, supra; Ausubel, 1995, supra.)

Genes encoding HUCYP can be turned off by transforming a cell or tissue with expression vectors which express high levels of a polynucleotide, or fragment thereof, encoding HUCYP. Such constructs may be used to introduce untranslatable sense or antisense sequences into a cell. Even in the absence of integration into the DNA, such vectors may continue to transcribe RNA molecules until they are disabled by endogenous nucleases. Transient expression may last for a month or more with a non-replicating vector, and may last even longer if appropriate replication elements are part of the vector system.

As mentioned above, modifications of gene expression can be obtained by designing complementary sequences or antisense molecules (DNA, RNA, or PNA) to the control, 5', or regulatory regions of the gene encoding HUCYP. Oligonucleotides derived from the transcription initiation site, e.g., between about positions −10 and +10 from the start site, are preferred. Similarly, inhibition can be achieved using triple helix base-pairing methodology. Triple helix pairing is useful because it causes inhibition of the ability of the double helix to open sufficiently for the binding of polymerases, transcription factors, or regulatory molecules. Recent therapeutic advances using triplex DNA have been described in the literature. (See, e.g., Gee, J. E. et al. (1994) in Huber, B. E. and B. I. Carr, *Molecular and Immunologic Approaches*, Futura Publishing, Mt. Kisco N.Y., pp. 163–177.) A complementary sequence or antisense molecule may also be designed to block translation of mRNA by preventing the transcript from binding to ribosomes.

Ribozymes, enzymatic RNA molecules, may also be used to catalyze the specific cleavage of RNA. The mechanism of ribozyme action involves sequence-specific hybridization of the ribozyme molecule to complementary target RNA, followed by endonucleolytic cleavage. For example, engineered hammerhead motif ribozyme molecules may specifically and efficiently catalyze endonucleolytic cleavage of sequences encoding HUCYP.

Specific ribozyme cleavage sites within any potential RNA target are initially identified by scanning the target molecule for ribozyme cleavage sites, including the following sequences: GUA, GUU, and GUC. Once identified, short RNA sequences of between 15 and 20 ribonucleotides, corresponding to the region of the target gene containing the cleavage site, may be evaluated for secondary structural features which may render the oligonucleotide inoperable. The suitability of candidate targets may also be evaluated by testing accessibility to hybridization with complementary oligonucleotides using ribonuclease protection assays.

Complementary ribonucleic acid molecules and ribozymes of the invention may be prepared by any method known in the art for the synthesis of nucleic acid molecules. These include techniques for chemically synthesizing oligonucleotides such as solid phase phosphoramidite chemical synthesis. Alternatively, RNA molecules may be generated by in vitro and in vivo transcription of DNA sequences encoding HUCYP. Such DNA sequences may be incorporated into a wide variety of vectors with suitable RNA polymerase promoters such as T7 or SP6. Alternatively, these cDNA constructs that synthesize complementary RNA, constitutively or inducibly, can be introduced into cell lines, cells, or tissues.

RNA molecules may be modified to increase intracellular stability and half-life. Possible modifications include, but are not limited to, the addition of flanking sequences at the 5' and/or 3' ends of the molecule, or the use of phosphorothioate or 2' O-methyl rather than phosphodiesterase linkages within the backbone of the molecule. This concept is inherent in the production of PNAs and can be extended in all of these molecules by the inclusion of nontraditional bases such as inosine, queosine, and wybutosine, as well as acetyl-, methyl-, thio-, and similarly modified forms of adenine, cytidine, guanine, thymine, and uridine which are not as easily recognized by endogenous endonucleases.

Many methods for introducing vectors into cells or tissues are available and equally suitable for use in vivo, in vitro, and ex vivo. For ex vivo therapy, vectors may be introduced into stem cells taken from the patient and clonally propagated for autologous transplant back into that same patient. Delivery by transfection, by liposome injections, or by polycationic amino polymers may be achieved using methods which are well known in the art. (See, e.g., Goldman, C. K. et al. (1997) Nature Biotechnology 15:462–466.)

Any of the therapeutic methods described above may be applied to any subject in need of such therapy, including, for example, mammals such as dogs, cats, cows, horses, rabbits, monkeys, and most preferably, humans.

An additional embodiment of the invention relates to the administration of a pharmaceutical or sterile composition, in conjunction with a pharmaceutically acceptable carrier, for any of the therapeutic effects discussed above. Such pharmaceutical compositions may consist of HUCYP, antibodies to HUCYP, and mimetics, agonists, antagonists, or inhibitors of HUCYP. The compositions may be administered alone or in combination with at least one other agent, such as a stabilizing compound, which may be administered in any sterile, biocompatible pharmaceutical carrier including, but not limited to, saline, buffered saline, dextrose, and water. The compositions may be administered to a patient alone, or in combination with other agents, drugs, or hormones.

The pharmaceutical compositions utilized in this invention may be administered by any number of routes including, but not limited to, oral, intravenous, intramuscular, intra-arterial, intramedullary, intrathecal, intraventricular, transdermal, subcutaneous, intraperitoneal, intranasal, enteral, topical, sublingual, or rectal means.

In addition to the active ingredients, these pharmaceutical compositions may contain suitable pharmaceutically-acceptable carriers comprising excipients and auxiliaries which facilitate processing of the active compounds into preparations which can be used pharmaceutically. Further details on techniques for formulation and administration may be found in the latest edition of *Remington's Pharmaceutical Sciences* (Maack Publishing, Easton Pa.).

Pharmaceutical compositions for oral administration can be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions, and the like, for ingestion by the patient.

Pharmaceutical preparations for oral use can be obtained through combining active compounds with solid excipient and processing the resultant mixture of granules (optionally, after grinding) to obtain tablets or dragee cores. Suitable auxiliaries can be added, if desired. Suitable excipients include carbohydrate or protein fillers, such as sugars, including lactose, sucrose, mannitol, and sorbitol; starch from corn, wheat, rice, potato, or other plants; cellulose, such as methyl cellulose, hydroxypropylmethyl-cellulose, or sodium carboxymethylcellulose; gums, including arabic and tragacanth; and proteins, such as gelatin and collagen. If desired, disintegrating or solubilizing agents may be added, such as the cross-linked polyvinyl pyrrolidone, agar, and alginic acid or a salt thereof, such as sodium alginate.

Dragee cores may be used in conjunction with suitable coatings, such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound, i.e., dosage.

Pharmaceutical preparations which can be used orally include push-fit capsules made of gelatin, as well as soft, sealed capsules made of gelatin and a coating, such as glycerol or sorbitol. Push-fit capsules can contain active ingredients mixed with fillers or binders, such as lactose or starches, lubricants, such as talc or magnesium stearate, and, optionally, stabilizers. In soft capsules, the active compounds may be dissolved or suspended in suitable liquids, such as fatty oils, liquid, or liquid polyethylene glycol with or without stabilizers.

Pharmaceutical formulations suitable for parenteral administration may be formulated in aqueous solutions, preferably in physiologically compatible buffers such as Hanks' solution, Ringer's solution, or physiologically buffered saline. Aqueous injection suspensions may contain substances which increase the viscosity of the suspension, such as sodium carboxymethyl cellulose, sorbitol, or dextran. Additionally, suspensions of the active compounds may be prepared as appropriate oily injection suspensions. Suitable lipophilic solvents or vehicles include fatty oils, such as sesame oil, or synthetic fatty acid esters, such as ethyl oleate, triglycerides, or liposomes. Non-lipid polycationic amino polymers may also be used for delivery. Optionally, the suspension may also contain suitable stabilizers or agents to increase the solubility of the compounds and allow for the preparation of highly concentrated solutions.

For topical or nasal administration, penetrants appropriate to the particular barrier to be permeated are used in the formulation. Such penetrants are generally known in the art.

The pharmaceutical compositions of the present invention may be manufactured in a manner that is known in the art, e.g., by means of conventional mixing, dissolving, granulating, dragee-making, levigating, emulsifying, encapsulating, entrapping, or lyophilizing processes.

The pharmaceutical composition may be provided as a salt and can be formed with many acids, including but not limited to, hydrochloric, sulfuric, acetic, lactic, tartaric, malic, and succinic acids. Salts tend to be more soluble in aqueous or other protonic solvents than are the corresponding free base forms. In other cases, the preferred preparation may be a lyophilized powder which may contain any or all of the following: 1 mM to 50 mM histidine, 0.1% to 2% sucrose, and 2% to 7% mannitol, at a pH range of 4.5 to 5.5, that is combined with buffer prior to use.

After pharmaceutical compositions have been prepared, they can be placed in an appropriate container and labeled for treatment of an indicated condition. For administration of HUCYP, such labeling would include amount, frequency, and method of administration.

Pharmaceutical compositions suitable for use in the invention include compositions wherein the active ingredients are contained in an effective amount to achieve the intended purpose. The determination of an effective dose is well within the capability of those skilled in the art.

For any compound, the therapeutically effective dose can be estimated initially either in cell culture assays, e.g., of neoplastic cells or in animal models such as mice, rats, rabbits, dogs, or pigs. An animal model may also be used to determine the appropriate concentration range and route of administration. Such information can then be used to determine useful doses and routes for administration in humans.

A therapeutically effective dose refers to that amount of active ingredient, for example HUCYP or fragments thereof, antibodies of HUCYP, and agonists, antagonists or inhibitors of HUCYP, which ameliorates the symptoms or condition. Therapeutic efficacy and toxicity may be determined by standard pharmaceutical procedures in cell cultures or with experimental animals, such as by calculating the $ED_{50}$ (the dose therapeutically effective in 50% of the population) or $LD_{50}$ (the dose lethal to 50% of the population) statistics. The dose ratio of toxic to therapeutic effects is the therapeutic index, and it can be expressed as the $LD_{50}/ED_{50}$ ratio. Pharmaceutical compositions which exhibit large therapeutic indices are preferred. The data obtained from cell culture assays and animal studies are used to formulate a range of dosage for human use. The dosage contained in such compositions is preferably within a range of circulating concentrations that includes the $ED_{50}$ with little or no toxicity. The dosage varies within this range depending upon the dosage form employed, the sensitivity of the patient, and the route of administration.

The exact dosage will be determined by the practitioner, in light of factors related to the subject requiring treatment. Dosage and administration are adjusted to provide sufficient levels of the active moiety or to maintain the desired effect. Factors which may be taken into account include the severity of the disease state, the general health of the subject, the age, weight, and gender of the subject, time and frequency of administration, drug combination(s), reaction sensitivities, and response to therapy. Long-acting pharmaceutical compositions may be administered every 3 to 4 days, every week, or biweekly depending on the half-life and clearance rate of the particular formulation.

Normal dosage amounts may vary from about 0.1 μg to 100,000 μg, up to a total dose of about 1 gram, depending upon the route of administration. Guidance as to particular dosages and methods of delivery is provided in the literature and generally available to practitioners in the art. Those skilled in the art will employ different formulations for nucleotides than for proteins or their inhibitors. Similarly, delivery of polynucleotides or polypeptides will be specific to particular cells, conditions, locations, etc.

Diagnostics

In another embodiment, antibodies which specifically bind HUCYP may be used for the diagnosis of disorders characterized by expression of HUCYP, or in assays to monitor patients being treated with HUCYP or agonists, antagonists, or inhibitors of HUCYP. Antibodies useful for diagnostic purposes may be prepared in the same manner as described above for therapeutics. Diagnostic assays for HUCYP include methods which utilize the antibody and a label to detect HUCYP in human body fluids or in extracts of cells or tissues. The antibodies may be used with or without modification, and may be labeled by covalent or non-covalent attachment of a reporter molecule. A wide variety of reporter molecules, several of which are described above, are known in the art and may be used.

A variety of protocols for measuring HUCYP, including ELISAs, RIAs, and FACS, are known in the art and provide a basis for diagnosing altered or abnormal levels of HUCYP expression. Normal or standard values for HUCYP expression are established by combining body fluids or cell extracts taken from normal mammalian subjects, preferably human, with antibody to HUCYP under conditions suitable for complex formation. The amount of standard complex formation may be quantitated by various methods, preferably by photometric means. Quantities of HUCYP expressed in subject samples, control and disease from biopsied tissues are compared with the standard values. Deviation between standard and subject values establishes the parameters for diagnosing disease.

In another embodiment of the invention, the polynucleotides encoding HUCYP may be used for diagnostic purposes. The polynucleotides which may be used include oligonucleotide sequences, complementary RNA and DNA molecules, and PNAs. The polynucleotides may be used to detect and quantitate gene expression in biopsied tissues in which expression of HUCYP may be correlated with disease. The diagnostic assay may be used to determine absence, presence, and excess expression of HUCYP, and to monitor regulation of HUCYP levels during therapeutic intervention.

In one aspect, hybridization with PCR probes which are capable of detecting polynucleotide sequences, including genomic sequences, encoding HUCYP or closely related molecules may be used to identify nucleic acid sequences which encode HUCYP. The specificity of the probe, whether it is made from a highly specific region, e.g., the 5' regulatory region, or from a less specific region, e.g., a conserved motif, and the stringency of the hybridization or amplification (maximal, high, intermediate, or low), will determine whether the probe identifies only naturally occurring sequences encoding HUCYP, allelic variants, or related sequences.

Probes may also be used for the detection of related sequences, and should preferably have at least 50% sequence identity to any of the HUCYP encoding sequences. The hybridization probes of the subject invention may be DNA or RNA and may be derived from the sequence of SEQ ID NO:2 or from genomic sequences including promoters, enhancers, and introns of the HUCYP gene.

Means for producing specific hybridization probes for DNAs encoding HUCYP include the cloning of polynucleotide sequences encoding HUCYP or HUCYP derivatives into vectors for the production of mRNA probes. Such vectors are known in the art, are commercially available, and may be used to synthesize RNA probes in vitro by means of the addition of the appropriate RNA polymerases and the appropriate labeled nucleotides. Hybridization probes may be labeled by a variety of reporter groups, for example, by radionuclides such as $^{32}$P or 35S, or by enzymatic labels, such as alkaline phosphatase coupled to the probe via avidin/biotin coupling systems, and the like.

Polynucleotide sequences encoding HUCYP may be used for the diagnosis of disorders associated with expression of HUCYP. Examples of such disorders include, but are not limited to, a cell proliferative disorder such as actinic keratosis, arteriosclerosis, atherosclerosis, bursitis, cirrhosis, hepatitis, mixed connective tissue disease (MCTD), myelofibrosis, paroxysmal nocturnal hemoglobinuria, polycythemia vera, psoriasis, primary thrombocythemia, and cancers including adenocarcinoma, leukemia, lymphoma, melanoma, myeloma, sarcoma, teratocarcinoma, and, in particular, cancers of the adrenal gland, bladder, bone, bone marrow, brain, breast, cervix, gall bladder, ganglia, gastrointestinal tract, heart, kidney, liver, lung, muscle, ovary, pancreas, parathyroid, penis, prostate, salivary glands, skin, spleen, testis, thymus, thyroid, and uterus; a developmental disorder such as renal tubular acidosis, anemia, Cushing's syndrome, achondroplastic dwarfism, Duchenne and Becker muscular dystrophy, epilepsy, gonadal dysgenesis, WAGR syndrome (Wilms' tumor, aniridia, genitourinary abnormalities, and mental retardation), Smith-Magenis syndrome, myelodysplastic syndrome, hereditary mucoepithelial dysplasia, hereditary keratodermas, hereditary neuropathies such as Charcot-Marie-Tooth disease and neurofibromatosis, hypothyroidism, hydrocephalus, seizure disorders such as Syndenham's chorea and cerebral palsy, spina bifida, anencephaly, craniorachischisis, congenital glaucoma, cataract, and sensorineural hearing loss; an autoimmune/inflammatory disorder such as acquired immunodeficiency syndrome (AIDS), Addison's disease, adult respiratory distress syndrome, allergies, ankylosing spondylitis, amyloidosis, anemia, asthma, atherosclerosis, autoimmune hemolytic anemia, autoimmune thyroiditis, autoimmune polyenodocrinopathy-candidiasis-ectodermal dystrophy (APECED), bronchitis, cholecystitis, contact dermatitis, Crohn's disease, atopic dermatitis, dermatomyositis, diabetes mellitus, emphysema, episodic lymphopenia with lymphocytotoxins, erythroblastosis fetalis, erythema nodosum, atrophic gastritis, glomerulonephritis, Goodpasture's syndrome, gout, Graves' disease, Hashimoto's thyroiditis, hypereosinophilia, irritable bowel syndrome, multiple sclerosis, myasthenia gravis, myocardial or pericardial inflammation, osteoarthritis, osteoporosis, pancreatitis, polymyositis, psoriasis, Reiter's syndrome, rheumatoid arthritis, scleroderma, Sjögren's syndrome, systemic anaphylaxis, systemic lupus erythematosus, systemic sclerosis, thrombocytopenic purpura, ulcerative colitis, uveitis, Werner syndrome, complications of cancer, hemodialysis, and extracorporeal circulation, viral, bacterial, fungal, parasitic, protozoal, and helminthic infections, and trauma; and a metabolic disorder such as Addison's disease, cystic fibrosis, diabetes, fatty hepatocirrhosis, galactosemia, goiter, hyperadrenalism, hypoadrenalism, hyperparathyroidism, hypoparathyroidism, hypercholesterolemia, hyperthyroidism, hypothyroidism hyperlipidemia, hyperlipemia, lipid myopathies, obesity, lipodystrophies, and phenylketonuria, congenital adrenal hyperplasia, pseudovitamin D-deficiency rickets, cerebrotendinous xanthomatosis, and coumarin resistance. The polynucleotide sequences encoding HUCYP may be used in Southern or northern analysis, dot blot, or other membrane-based technologies; in PCR technologies; in dipstick, pin, and multiformat ELISA-like assays; and in microarrays utilizing fluids or tissues from patients to detect altered HUCYP expression. Such qualitative or quantitative methods are well known in the art.

In a particular aspect, the nucleotide sequences encoding HUCYP may be useful in assays that detect the presence of associated disorders, particularly those mentioned above. The nucleotide sequences encoding HUCYP may be labeled by standard methods and added to a fluid or tissue sample from a patient under conditions suitable for the formation of hybridization complexes. After a suitable incubation period, the sample is washed and the signal is quantitated and compared with a standard value. If the amount of signal in the patient sample is significantly altered in comparison to a control sample then the presence of altered levels of nucleotide sequences encoding HUCYP in the sample indicates the presence of the associated disorder. Such assays may also be used to evaluate the efficacy of a particular therapeutic treatment regimen in animal studies, in clinical trials, or to monitor the treatment of an individual patient.

In order to provide a basis for the diagnosis of a disorder associated with expression of HUCYP, a normal or standard profile for expression is established. This may be accomplished by combining body fluids or cell extracts taken from normal subjects, either animal or human, with a sequence, or a fragment thereof, encoding HUCYP, under conditions suitable for hybridization or amplification. Standard hybridization may be quantified by comparing the values obtained from normal subjects with values from an experiment in which a known amount of a substantially purified polynucleotide is used. Standard values obtained in this manner may be compared with values obtained from samples from patients who are symptomatic for a disorder. Deviation from standard values is used to establish the presence of a disorder.

Once the presence of a disorder is established and a treatment protocol is initiated, hybridization assays may be repeated on a regular basis to determine if the level of expression in the patient begins to approximate that which is observed in the normal subject. The results obtained from successive assays may be used to show the efficacy of treatment over a period ranging from several days to months.

With respect to cancer, the presence of an abnormal amount of transcript (either under- or over-expressed) in biopsied tissue from an individual may indicate a predisposition for the development of the disease, or may provide a means for detecting the disease prior to the appearance of actual clinical symptoms. A more definitive diagnosis of this type may allow health professionals to employ preventative measures or aggressive treatment earlier thereby preventing the development or further progression of the cancer.

Additional diagnostic uses for oligonucleotides designed from the sequences encoding HUCYP may involve the use of PCR. These oligomers may be chemically synthesized, generated enzymatically, or produced in vitro. Oligomers will preferably contain a fragment of a polynucleotide encoding HUCYP, or a fragment of a polynucleotide complementary to the polynucleotide encoding HUCYP, and will be employed under optimized conditions for identification of a specific gene or condition. Oligomers may also be employed under less stringent conditions for detection or quantitation of closely related DNA or RNA sequences.

Methods which may also be used to quantitate the expression of HUCYP include radiolabeling or biotinylating nucleotides, coamplification of a control nucleic acid, and interpolating results from standard curves. (See, e.g., Melby, P. C. et al. (1993) J. Immunol. Methods 159:235–244; Duplaa, C. et al. (1993) Anal. Biochem. 229–236.) The speed of quantitation of multiple samples may be accelerated by running the assay in an ELISA format where the oligomer of interest is presented in various dilutions and a spectrophotometric or colorimetric response gives rapid quantitation.

In further embodiments, oligonucleotides or longer fragments derived from any of the polynucleotide sequences described herein may be used as targets in a microarray. The microarray can be used to monitor the expression level of large numbers of genes simultaneously and to identify genetic variants, mutations, and polymorphisms. This information may be used to determine gene function, to understand the genetic basis of a disorder, to diagnose a disorder, and to develop and monitor the activities of therapeutic agents.

Microarrays may be prepared, used, and analyzed using methods known in the art. (See, e.g., Brennan, T. M. et al. (1995) U.S. Pat. No. 5,474,796; Schena, M. et al. (1996) Proc. Natl. Acad. Sci. 93:10614–10619; Baldeschweiler et al. (1995) PCT application WO95/251116; Shalon, D. et al. (1995) PCT application WO95/35505; Heller, R. A. et al. (1997) Proc. Natl. Acad. Sci. 94:2150–2155; and Heller, M. J. et al. (1997) U.S. Pat. No. 5,605,662.)

In another embodiment of the invention, nucleic acid sequences encoding HUCYP may be used to generate hybridization probes useful in mapping the naturally occurring genomic sequence. The sequences may be mapped to a particular chromosome, to a specific region of a chromosome, or to artificial chromosome constructions, e.g., human artificial chromosomes (HACs), yeast artificial chromosomes (YACs), bacterial artificial chromosomes (BACs), bacterial P1 constructions, or single chromosome cDNA libraries. (See, e.g., Harrington, J. J. et al. (1997) Nat Genet. 15:345–355; Price, C. M. (1993) Blood Rev. 7:127–134; and Trask, B. J. (1991) Trends Genet. 7:149–154.)

Fluorescent in situ hybridization (FISH) may be correlated with other physical chromosome mapping techniques and genetic map data. (See, e.g., Heinz-Ulrich, et al. (1995) in Meyers, supra, pp. 965–968.) Examples of genetic map data can be found in various scientific journals or at the Online Mendelian Inheritance in Man (OMIM) site. Correlation between the location of the gene encoding HUCYP on a physical chromosomal map and a specific disorder, or a predisposition to a specific disorder, may help define the region of DNA associated with that disorder. The nucleotide sequences of the invention may be used to detect differences in gene sequences among normal, carrier, and affected individuals.

In situ hybridization of chromosomal preparations and physical mapping techniques, such as linkage analysis using established chromosomal markers, may be used for extending genetic maps. Often the placement of a gene on the chromosome of another mammalian species, such as mouse, may reveal associated markers even if the number or arm of a particular human chromosome is not known. New sequences can be assigned to chromosomal arms by physical mapping. This provides valuable information to investigators searching for disease genes using positional cloning or other gene discovery techniques. Once the disease or syndrome has been crudely localized by genetic linkage to a particular genomic region, e.g., ataxia-telangiectasia to 11q22–23, any sequences mapping to that area may represent associated or regulatory genes for further investigation. (See, e.g., Gatti, R. A. et al. (1988) Nature 336:577–580.) The nucleotide sequence of the subject invention may also be used to detect differences in the chromosomal location due to translocation, inversion, etc., among normal, carrier, or affected individuals.

In another embodiment of the invention, HUCYP, its catalytic or immunogenic fragments, or oligopeptides thereof can be used for screening libraries of compounds in any of a variety of drug screening techniques. The fragment employed in such screening may be free in solution, affixed to a solid support, borne on a cell surface, or located intracellularly. The formation of binding complexes between HUCYP and the agent being tested may be measured.

Another technique for drug screening provides for high throughput screening of compounds having suitable binding affinity to the protein of interest. (See, e.g., Geysen, et al. (1984) PCT application WO84/03564.) In this method, large numbers of different small test compounds are synthesized on a solid substrate. The test compounds are reacted with HUCYP, or fragments thereof, and washed. Bound HUCYP is then detected by methods well known in the art. Purified HUCYP can also be coated directly onto plates for use in the aforementioned drug screening techniques. Alternatively, non-neutralizing antibodies can be used to capture the peptide and immobilize it on a solid support.

In another embodiment, one may use competitive drug screening assays in which neutralizing antibodies capable of binding HUCYP specifically compete with a test compound for binding HUCYP. In this manner, antibodies can be used to detect the presence of any peptide which shares one or more antigenic determinants with HUCYP.

In additional embodiments, the nucleotide sequences which encode HUCYP may be used in any molecular biology techniques that have yet to be developed, provided the new techniques rely on properties of nucleotide sequences that are currently known, including, but not limited to, such properties as the triplet genetic code and specific base pair interactions.

The examples below are provided to illustrate the subject invention and are not included for the purpose of limiting the invention.

EXAMPLES

I. cDNA Library Construction

The COLNNOT11 cDNA library was constructed from microscopically normal colon tissue obtained from a 60-year-old Caucasian male who had undergone a left hemicolectomy to remove grade 3 (of 4) adenocarcinoma in a different part of his bowel. The patient history reported previous diagnoses of depressive disorder and thrombophlebitis, accompanied by inflammatory polyarthropathies and inflammatory disease of the prostate.

The frozen tissue was homogenized and lysed using a Polytron PT-3000 homogenizer (Brinkmann Instruments, Westbury N.J.) in guanidinium isothiocyanate solution. The lysate was centrifuged over a 5.7 M CsCl cushion using a SW28 rotor in a L8-70M ultracentrifuge (Beckman Instruments, Fullerton Calif.) for 18 hours at 25,000 rpm at ambient temperature. The RNA was extracted with acid phenol pH 4.0, precipitated using 0.3 M sodium acetate and 2.5 volumes of ethanol, resuspended in RNAse-free water and treated with DNase at 37° C. The RNA extraction and precipitation were repeated as before. The mRNA was isolated using an OLIGOTEX kit (QIAGEN, Valencia Calif.) and used to construct the cDNA library.

The mRNA was handled according to the recommended protocols in the SUPERSCRIPT plasmid system (Life Technologies). cDNAs were fractionated on a SEPHAROSE CL4B column (Amersham Pharmacia Biotech), and those cDNAs exceeding 400 bp were ligated into pSPORT1 plasmid (Life Technologies). The plasmid pSport I was subsequently transformed into DH5α competent cells (Life Technologies).

II. Isolation of cDNA Clones

Plasmid DNA was released from the cells and purified using the R.E.A.L. PREP 96 plasmid kit from QIAGEN. This kit enables the simultaneous purification of 96 samples in a 96-well block using multi-channel reagent dispensers. The recommended protocol was employed except for the following changes: 1) the bacteria were cultured in 1 ml of sterile Terrific Broth (Life Technologies) with carbenicillin at 25 mg/L and glycerol at 0.4%; 2) after inoculation, the cultures were incubated for 19 hours and at the end of incubation, the cells were lysed with 0.3 ml of lysis buffer; and 3) following isopropanol precipitation, the plasmid DNA pellet was resuspended in 0.1 ml of distilled water. After the last step in the protocol, samples were transferred to a 96-well block for storage at 4° C.

III. Sequencing and Analysis

The cDNAs were prepared for sequencing using the ABI CATALYST 800 (Perkin-Elmer) or the HYDRA microdispenser (Robbins Scientific) or MICROLAB 2200 (Hamilton) systems in combination with PTC-200 thermal cyclers (MJ Research). The cDNAs were sequenced using the ABI PRISM 373 or 377 sequencing systems (Perkin-Elmer) and standard ABI protocols, base calling software, and kits. In one alternative, cDNAs were sequenced using the MEGABACE 1000 DNA sequencing system (Molecular Dynamics). In another alternative, the cDNAs were amplified and sequenced using the ABI PRISM BIGDYE Terminator cycle sequencing ready reaction kit (Perkin-Elmer). In yet another alternative, cDNAs were sequenced using solutions and dyes from Amersham Pharmacia Biotech. Reading frames for the ESTs were determined using standard methods (reviewed in Ausubel, 1997, supra, unit 7.7). Some of the cDNA sequences were selected for extension using the techniques disclosed in Example V.

The polynucleotide sequences derived from cDNA, extension, and shotgun sequencing were assembled and analyzed using a combination of software programs which utilize algorithms well known to those skilled in the art. Table 1 summarizes the tools, programs, and algorithms used and provides descriptions, references, and threshold parameters when applicable. The first column of Table 1 shows the tools, programs, and algorithms used, the second column provides brief descriptions, the third column presents the appropriate references, all of which are incorporated by reference herein in their entirety, and the fourth column presents, where applicable, the scores, probability values, and other parameters used to evaluate the strength of a match between two sequences (the higher the score, the greater the homology between two sequences). Sequences were analyzed using MACDNASIS PRO software (Hitachi Software Engineering) and LASERGENE software (DNASTAR).

The polynucleotide sequences were validated by removing vector, linker, and polyA sequences and by masking ambiguous bases, using algorithms and programs based on BLAST, dynamic programming, and dinucleotide nearest neighbor analysis. The sequences were then queried against a selection of public databases, such as the GenBank primate, rodent, mammalian, vertebrate, and eukaryote databases, and BLOCKS to acquire annotation, using programs based on BLAST, FASTA, and BLIMPS. The sequences were assembled into full length polynucleotide sequences using programs based on Phred, Phrap, and Consed, and were screened for open reading frames using programs based on GeneMark, BLAST, and FASTA. The full length polynucleotide sequences were translated to derive the corresponding full length amino acid sequences, and these full length sequences were subsequently analyzed by querying against databases such as the GenBank databases, SwissProt, BLOCKS, PRINTS, PFAM, and Prosite.

The programs described above for the assembly and analysis of full length polynucleotide and amino acid sequences were used to identify polynucleotide sequence fragments from SEQ ID NO:2.

Fragments from about 20 to about 4000 nucleotides which are useful in hybridization and amplification technologies were described in the Invention section above.

IV. Northern Analysis

Northern analysis is a laboratory technique used to detect the presence of a transcript of a gene and involves the hybridization of a labeled nucleotide sequence to a membrane on which RNAs from a particular cell type or tissue have been bound. (See, e.g., Sambrook, supra, ch. 7; Ausubel, 1995, supra, ch. 4 and 16.)

Analogous computer techniques applying BLAST were used to search for identical or related molecules in nucleotide databases such as the GenBank or LIFESEQ databases (Incyte Pharmaceuticals, Palo Alto Calif.). This analysis is much faster than multiple membrane-based hybridizations. In addition, the sensitivity of the computer search can be modified to determine whether any particular match is categorized as exact or similar. The basis of the search is the product score, which is defined as:

$$\frac{\% \text{ sequence identity} \times \% \text{ maximum BLAST score}}{100}$$

The product score takes into account both the degree of similarity between two sequences and the length of the sequence match. For example, with a product score of 40, the match will be exact within a 1% to 2% error, and, with a product score of 70, the match will be exact. Similar molecules are usually identified by selecting those which show product scores between 15 and 40, although lower scores may identify related molecules.

The results of northern analyses reported a percentage distribution of libraries in which the transcript encoding HUCYP occurred. Analysis involved the categorization of cDNA libraries by organ/tissue and disease. The organ/tissue categories included cardiovascular, dermatologic, developmental, endocrine, gastrointestinal, hematopoietic/immune, musculoskeletal, nervous, reproductive, and urologic. The disease categories included cancer, inflammation/trauma, fetal, neurological, and pooled. For each category, the number of libraries expressing the sequence of interest was counted and divided by the total number of libraries across all categories. Percentage values of tissue-specific and disease expression are reported in the description of the invention.

V. Extension of HUCYP Encoding Polynucleotides

The full length nucleic acid sequence of SEQ ID NO:2 was produced by extension of an appropriate fragment of the full length molecule using oligonucleotide primers designed from this fragment. One primer was synthesized to initiate 5' extension of the known fragment, and the other primer, to initiate 3' extension of the known fragment. The initial primers were designed using OLIGO 4.06 software (National Biosciences), or another appropriate program, to be about 22 to 30 nucleotides in length, to have a GC content of about 50% or more, and to anneal to the target sequence at temperatures of about 68° C. to about 72° C. Any stretch of nucleotides which would result in hairpin structures and primer-primer dimerizations was avoided.

Selected human cDNA libraries were used to extend the sequence. If more than one extension was necessary or desired, additional or nested sets of primers were designed.

High fidelity amplification was obtained by PCR using methods well known in the art. PCR was performed in 96-well plates using the PTC-200 thermal cycler (MJ Research, Inc.). The reaction mix contained DNA template, 200 nmol of each primer, reaction buffer containing $Mg^{2+}$, $(NH_4)_2SO_4$, and β-mercaptoethanol, Taq DNA polymerase (Amersham Pharmacia Biotech), ELONGASE enzyme (Life Technologies), and Pfu DNA polymerase (Stratagene), with the following parameters for primer pair PCI A and PCI B: Step 1: 94° C., 3 min; Step 2: 94° C., 15 sec; Step 3: 60° C., 1 min; Step 4: 68° C., 2 min; Step 5: Steps 2, 3, and 4 repeated 20 times; Step 6: 68° C., 5 min; Step 7: storage at 4° C. In the alternative, the parameters for primer pair T7 and SK+ were as follows: Step 1: 94° C., 3 min; Step 2: 94° C., 15 sec; Step 3: 57° C., 1 min; Step 4: 68° C., 2 min; Step 5: Steps 2, 3, and 4 repeated 20 times; Step 6: 68° C., 5 min; Step 7: storage at 4° C.

The concentration of DNA in each well was determined by dispensing 100 μl PICO GREEN quantitation reagent (0.25% (v/v) PICO GREEN; Molecular Probes, Eugene Org.) dissolved in 1X TE and 0.5 μl of undiluted PCR product into each well of an opaque fluorimeter plate (Corning Costar, Acton Mass.), allowing the DNA to bind to the reagent. The plate was scanned in a Fluoroskan II (Labsystems Oy, Helsinki, Finland) to measure the fluorescence of the sample and to quantify the concentration of DNA. A 5 μl to 10 μl aliquot of the reaction mixture was analyzed by electrophoresis on a 1% agarose mini-gel to determine which reactions were successful in extending the sequence.

The extended nucleotides were desalted and concentrated, transferred to 384-well plates, digested with CviJI cholera virus endonuclease (Molecular Biology Research, Madison Wis.), and sonicated or sheared prior to religation into pUC 18 vector (Amersham Pharmacia Biotech). For shotgun sequencing, the digested nucleotides were separated on low concentration (0.6 to 0.8%) agarose gels, fragments were excised, and agar digested with Agar ACE (Promega). Extended clones were religated using T4 ligase (New England Biolabs, Beverly Mass.) into pUC 18 vector (Amersham Pharmacia Biotech), treated with Pfu DNA polymerase (Stratagene) to fill-in restriction site overhangs, and transfected into competent *E. coli* cells. Transformed cells were selected on antibiotic-containing media, individual colonies were picked and cultured overnight at 37° C. in 384-well plates in LB/2x carb liquid media.

The cells were lysed, and DNA was amplified by PCR using Taq DNA polymerase (Amersham Pharmacia Biotech) and Pfu DNA polymerase (Stratagene) with the following parameters: Step 1: 94° C., 3 min; Step 2: 94° C., 15 sec; Step 3: 60° C., I min; Step 4: 72° C., 2 min; Step 5: step 2, 3, and 4 repeated 29 times; Step 6: 72° C., 5 min; Step 7: storage at 4° C. DNA was quantified by PICOGREEN reagent (Molecular Probes) as described above. Samples with low DNA recoveries were reamplified using the same conditions as described above. Samples were diluted with 20% dimethysulphoxide (1:2, v/v), and sequenced using DYENAMIC energy transfer sequencing primers and the DYENAMIC DIRECT kit (Amersham Pharmacia Biotech) or the ABI PRISM BIGDYE Terminator cycle sequencing ready reaction kit (Perkin-Elmer).

In like manner, the nucleotide sequence of SEQ ID NO:2 is used to obtain 5' regulatory sequences using the procedure above, oligonucleotides designed for such extension, and an appropriate genomic library.

VI. Labeling and Use of Individual Hybridization Probes

Hybridization probes derived from SEQ ID NO:2 are employed to screen cDNAs, genomic DNAs, or mRNAs. Although the labeling of oligonucleotides, consisting of about 20 base pairs, is specifically described, essentially the same procedure is used with larger nucleotide fragments. Oligonucleotides are designed using state-of-the-art software such as OLIGO 4.06 software (National Biosciences) and labeled by combining 50 pmol of each oligomer, 250 $\mu$Ci of [$^{32}$P]-adenosine triphosphate (Amersham Pharmacia Biotech), and T4 polynucleotide kinase (DuPont NEN, Boston Mass.). The labeled oligonucleotides are substantially purified using a SEPHADEX G-25 superfine size exclusion dextran bead column (Amersham Pharmacia Biotech). An aliquot containing $10^7$ counts per minute of the labeled probe is used in a typical membrane-based hybridization analysis of human genomic DNA digested with one of the following endonucleases: Ase I, Bgl II, Eco RI, Pst I, Xbal, or Pvu II (DuPont NEN).

The DNA from each digest is fractionated on a 0.7% agarose gel and transferred to nylon membranes (Nytran Plus, Schleicher & Schuell, Durham N.H.). Hybridization is carried out for 16 hours at 40° C. To remove nonspecific signals, blots are sequentially washed at room temperature under increasingly stringent conditions up to 0.1×saline sodium citrate and 0.5% sodium dodecyl sulfate. Hybridization patterns are visualized and compared using autoradiography.

VII. Microarrays

A chemical coupling procedure and an ink jet device can be used to synthesize array elements on the surface of a substrate. (See, e.g., Baldeschweiler, supra.) An array analogous to a dot or slot blot may also be used to arrange and link elements to the surface of a substrate using thermal, UV, chemical, or mechanical bonding procedures. A typical array may be produced by hand or using available methods and machines and contain any appropriate number of elements. After hybridization, nonhybridized probes are removed and a scanner used to determine the levels and patterns of fluorescence. The degree of complementarity and the relative abundance of each probe which hybridizes to an element on the microarray may be assessed through analysis of the scanned images.

Full-length cDNAs, Expressed Sequence Tags (ESTs), or fragments thereof may comprise the elements of the microarray. Fragments suitable for hybridization can be selected using software well known in the art such as LASERGENE software (DNASTAR). Full-length cDNAs, ESTs, or fragments thereof corresponding to one of the nucleotide sequences of the present invention, or selected at random from a cDNA library relevant to the present invention, are arranged on an appropriate substrate, e.g., a glass slide. The cDNA is fixed to the slide using, e.g., UV cross-linking followed by thermal and chemical treatments and subsequent drying. (See, e.g., Schena, M. et al. (1995) Science 270:467–470; Shalon, D. et al. (1996) Genome Res. 6:639–645.) Fluorescent probes are prepared and used for hybridization to the elements on the substrate. The substrate is analyzed by procedures described above.

VIII. Complementary Polynucleotides

Sequences complementary to the HUCYP-encoding sequences, or any parts thereof, are used to detect, decrease, or inhibit expression of naturally occurring HUCYP. Although use of oligonucleotides comprising from about 15 to 30 base pairs is described, essentially the same procedure is used with smaller or with larger sequence fragments. Appropriate oligonucleotides are designed using OLIGO 4.06 software (National Biosciences) and the coding sequence of HUCYP. To inhibit transcription, a complementary oligonucleotide is designed from the most unique 5' sequence and used to prevent promoter binding to the coding sequence. To inhibit translation, a complementary oligonucleotide is designed to prevent ribosomal binding to the HUCYP-encoding transcript.

IX. Expression of HUCYP

Expression and purification of HUCYP are achieved using bacterial or virus-based expression systems. For expression of HUCYP in bacteria, cDNA is subcloned into an appropriate vector containing an antibiotic resistance gene and an inducible promoter that directs high levels of cDNA transcription. Examples of such promoters include, but are not limited to, the trp-lac (tac) hybrid promoter and the T5 or T7 bacteriophage promoter in conjunction with the lac operator regulatory element. Recombinant vectors are transformed into suitable bacterial hosts, e.g., BL21(DE3). Antibiotic resistant bacteria express HUCYP upon induction with isopropyl beta-D-thiogalactopyranoside (IPTG). Expression of HUCYP in eukaryotic cells is achieved by infecting insect or mammalian cell lines with recombinant *Autographica californica* nuclear polyhedrosis virus (AcMNPV), commonly known as baculovirus. The nonessential polyhedrin gene of baculovirus is replaced with cDNA encoding HUCYP by either homologous recombination or bacterial-mediated transposition involving transfer plasmid intermediates. Viral infectivity is maintained and the strong polyhedrin promoter drives high levels of cDNA transcription. Recombinant baculovirus is used to infect *Spodoptera frugiperda* (Sf9) insect cells in most cases, or human hepatocytes, in some cases. Infection of the latter requires additional genetic modifications to baculovirus. (See Engelhard, E. K. et al. (1994) Proc. Natl. Acad. Sci. USA 91:3224–25 3227; Sandig, V. et al. (1996) Hum. Gene Ther. 7:1937–1945.)

In most expression systems, HUCYP is synthesized as a fusion protein with, e.g., glutathione S-transferase (GST) or a peptide epitope tag, such as FLAG or 6-His, permitting rapid, single-step, affinity-based purification of recombinant fusion protein from crude cell lysates. GST, a 26-kilodalton enzyme from *Schistosoma japonicum*, enables the purification of fusion proteins on immobilized glutathione under conditions that maintain protein activity and antigenicity (Amersham Pharmacia Biotech). Following purification, the GST moiety can be proteolytically cleaved from HUCYP at specifically engineered sites. FLAG, an 8-amino acid peptide, enables immunoaffinity purification using commercially available monoclonal and polyclonal anti-FLAG antibodies (Eastman Kodak). 6-His, a stretch of six consecutive histidine residues, enables purification on metal-chelate resins (QIAGEN). Methods for protein expression and purification are discussed in Ausubel (1995, supra, ch 10 and 16). Purified HUCYP obtained by these methods can be used directly in the following activity assay.

X. Demonstration of HUCYP Activity

HUCYP activity is demonstrated as the ability to hydroxylate the steroid testosterone (Waxman, D. J. (1991) Methods Enzymol. 206:462–476). 4-$^{14}$C-testosterone is diluted with unlabeled testosterone dissolved in toluene to give a working solution of 5–7 mCi/mmol. Ten nanomoles of the working solution of 4-$^{14}$C-testosterone (final assay concentration 50 μM) are aliquoted to a 13×100 mm assay tube, and the solvent is evaporated under $N_2$. HUCYP, 0.1 M HEPES buffer, pH 7.4, and 0.1 mM EDTA are added to the tube, on ice, to give a final volume of 175 μl. A control tube is prepared that lacks HUCYP. Samples are vortexed briefly, and the tubes are transferred to a shaking 37° C. water bath. Reactions are initiated 4 minutes later by the addition of NADPH dissolved in 25 μl 0.1 M HEPES buffer, pH 7.4 to give a final NADPH concentration of 0.3 mM. Reactions are terminated after 10–20 minutes by the addition of 1 ml ethyl acetate and vortexed for 30 seconds. The hydroxylated products are separated from testosterone by thin layer chromatography and detected by autoradiography. Product migrations are compared with those of testosterone and of hydroxylated steroid standards to identify the products. Reaction products are cut out of the thin layer chromatography plate and counted in a liquid scintillation counter. The amount of hydroxylated steroid products found is proportional to HUCYP activity.

XI. Functional Assays

HUCYP function is assessed by expressing the sequences encoding HUCYP at physiologically elevated levels in mammalian cell culture systems. cDNA is subcloned into a mammalian expression vector containing a strong promoter that drives high levels of cDNA expression. Vectors of choice include pCMV SPORT (Life Technologies) and pCR3.1 (Invitrogen, Carlsbad Calif.), both of which contain the cytomegalovirus promoter. 5–10 μg of recombinant vector are transiently transfected into a human cell line, preferably of endothelial or hematopoietic origin, using either liposome formulations or electroporation. 1–2 μg of an additional plasmid containing sequences encoding a marker protein are co-transfected. Expression of a marker protein provides a means to distinguish transfected cells from nontransfected cells and is a reliable predictor of cDNA expression from the recombinant vector. Marker proteins of choice include, e.g., Green Fluorescent Protein (GFP; Clontech), CD64, or a CD64-GFP fusion protein.

Flow cytometry (FCM), an automated, laser optics-based technique, is used to identify transfected cells expressing GFP or CD64-GFP, and to evaluate cellular properties, for example, their apoptotic state. FCM detects and quantifies the uptake of fluorescent molecules that diagnose events preceding or coincident with cell death. These events include changes in nuclear DNA content as measured by staining of DNA with propidium iodide; changes in cell size and granularity as measured by forward light scatter and 90 degree side light scatter; down-regulation of DNA synthesis as measured by decrease in bromodeoxyuridine uptake; alterations in expression of cell surface and intracellular proteins as measured by reactivity with specific antibodies; and alterations in plasma membrane composition as measured by the binding of fluorescein-conjugated Annexin V protein to the cell surface. Methods in flow cytometry are discussed in Ormerod, M. G. (1994) *Flow Cytometry*, Oxford, New York N.Y.

The influence of HUCYP on gene expression can be assessed using highly purified populations of cells transfected with sequences encoding HUCYP and either CD64 or CD64-GFP. CD64 and CD64-GFP are expressed on the surface of transfected cells and bind to conserved regions of human immunoglobulin G (IgG). Transfected cells are efficiently separated from nontransfected cells using magnetic beads coated with either human IgG or antibody against CD64 (DYNAL, Lake Success N.Y.). mRNA can be purified from the cells using methods well known by those of skill in the art. Expression of mRNA encoding HUCYP and other genes of interest can be analyzed by northern analysis or microarray techniques.

XII. Production of HUCYP Specific Antibodies

HUCYP substantially purified using polyacrylamide gel electrophoresis (PAGE; see, e.g., Harrington, M. G. (1990) Methods Enzymol. 182:488–495), or other purification techniques, is used to immunize rabbits and to produce antibodies using standard protocols.

Alternatively, the HUCYP amino acid sequence is analyzed using LASERGENE software (DNASTAR) to determine regions of high immunogenicity, and a corresponding oligopeptide is synthesized and used to raise antibodies by means known to those of skill in the art. Methods for selection of appropriate epitopes, such as those near the C-terminus or in hydrophilic regions are well described in the art. (See, e.g., Ausubel, 1995, supra, ch. 11.)

Typically, oligopeptides 15 residues in length are synthesized using an ABI 431A Peptide Synthesizer (Perkin-Elmer) using fmoc-chemistry and coupled to KLH (Sigma-Aldrich, St. Louis Mo.) by reaction with N-maleimidobenzoyl-N-hydroxysuccinimide ester (MBS) to increase immunogenicity. (See, e.g., Ausubel, 1995, supra.) Rabbits are immunized with the oligopeptide-KLH complex in complete Freund's adjuvant. Resulting antisera are tested for antipeptide activity by, for example, binding the peptide to plastic, blocking with 1% BSA, reacting with rabbit antisera, washing, and reacting with radio-iodinated goat anti-rabbit IgG.

XIII. Purification of Naturally Occurring HUCYP Using Specific Antibodies

Naturally occurring or recombinant HUCYP is substantially purified by immunoaffinity chromatography using antibodies specific for HUCYP. An immunoaffinity column is constructed by covalently coupling anti-HUCYP antibody to an activated chromatographic resin, such as CNBractivated SEPHAROSE (Amersham Pharmacia Biotech). After the coupling, the resin is blocked and washed according to the manufacturer's instructions.

Media containing HUCYP are passed over the immunoaffinity column, and the column is washed under conditions that allow the preferential absorbance of HUCYP (e.g., high ionic strength buffers in the presence of detergent). The column is eluted under conditions that disrupt antibody/HUCYP binding (e.g., a buffer of pH 2 to pH 3, or a high concentration of a chaotrope, such as urea or thiocyanate ion), and HUCYP is collected.

XIV. Identification of Molecules Which Interact with HUCYP

HUCYP, or biologically active fragments thereof, are labeled with $^{125}$I Bolton-Hunter reagent. (See, e.g., Bolton et al. (1973) Biochem. J. 133:529–539.) Candidate molecules previously arrayed in the wells of a multi-well plate are incubated with the labeled HUCYP, washed, and any wells with labeled HUCYP complex are assayed. Data obtained using different concentrations of HUCYP are used to calculate values for the number, affinity, and association of HUCYP with the candidate molecules. Various modifications and variations of the described methods and systems of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

What is claimed is:

1. An isolated and purified polynucleotide encoding a polypeptide
   (a) comprising SEQ ID NO:1; or
   (b) consisting of a fragment of SEQ ID NO:1 from about amino acid residue Ala at position 25 to about amino acid residue Glu at position 39 of SEQ ID NO:1.

2. An isolated and purified polynucleotide having at least 85% polynucleotide sequence identity to the polynucleotide of claim 1(a) over the full length of the sequence.

3. An isolated and purified polynucleotide having a sequence which is complementary to the polynucleotide of claim 1.

4. An isolated and purified polynucleotide
   (a) comprising the polynucleotide sequence of SEQ ID NO:2; or
   (b) consisting of a fragment of SEQ ID NO:2 from about nucleotide 109 to about nucleotide 153 of SEQ ID NO:2.

5. An isolated and purified polynucleotide having at least 85% polynucleotide sequence identity to the polynucleotide of claim 4(a) over the full length of the sequence.

6. An isolated and purified polynucleotide having a sequence which is complementary to the polynucleotide of claim 4.

7. An expression vector comprising the polynucleotide of claim 1.

8. A host cell comprising the expression vector of claim 7.

9. A method for producing a polypeptide, the method comprising the steps of:
   (a) culturing the host cell of claim 8 under conditions suitable for the expression of the polypeptide; and
   (b) recovering the polypeptide from the host cell culture.

10. A method for detecting a polynucleotide, the method comprising the steps of:
    (a) hybridizing the polynucleotide of claim 3 to at least one nucleic acid in a sample, thereby forming a hybridization complex; and
    (b) detecting the hybridization complex, wherein the presence of the hybridization complex correlates with the presence of the polynucleotide in the sample.

11. The method of claim 10 further comprising amplifying the polynucleotide prior to hybridization.

* * * * *